(12) United States Patent
Emrick

(10) Patent No.: US 8,802,738 B2
(45) Date of Patent: Aug. 12, 2014

(54) POLYESTERS WITH GRAFTED ZWITTERIONS

(75) Inventor: Todd Emrick, South Deerfield, MA (US)

(73) Assignee: University of Massachusetts, Boston, MA (US)

( * ) Notice: Subject to any disclaimer, the term of this patent is extended or adjusted under 35 U.S.C. 154(b) by 188 days.

(21) Appl. No.: 13/131,662

(22) PCT Filed: Dec. 11, 2009

(86) PCT No.: PCT/US2009/067668
§ 371 (c)(1),
(2), (4) Date: Sep. 14, 2011

(87) PCT Pub. No.: WO2010/068864
PCT Pub. Date: Jun. 17, 2010

(65) Prior Publication Data
US 2011/0319570 A1    Dec. 29, 2011

Related U.S. Application Data

(60) Provisional application No. 61/122,065, filed on Dec. 12, 2008, provisional application No. 61/233,982, filed on Aug. 14, 2009.

(51) Int. Cl.
*A61K 47/34* (2006.01)
*C08G 63/08* (2006.01)

(52) U.S. Cl.
USPC ........ 514/772.1; 525/410; 525/415; 525/418; 525/450; 514/772.3; 514/772.7

(58) Field of Classification Search
USPC ............... 525/410, 415, 418, 450; 514/772.3, 514/772.7, 772.1
See application file for complete search history.

(56) References Cited

U.S. PATENT DOCUMENTS

| | | | | |
|---|---|---|---|---|
| 5,610,241 | A | * | 3/1997 | Lee et al. ...................... 525/411 |
| 6,592,899 | B2 | * | 7/2003 | Fowers et al. ................. 424/486 |
| 2007/0104654 | A1 | * | 5/2007 | Hsieh et al. .................... 424/46 |
| 2009/0018646 | A1 | * | 1/2009 | Zhao ............................ 623/1.43 |

FOREIGN PATENT DOCUMENTS

EP    2014308 A2    1/2009

OTHER PUBLICATIONS

Parrish, Bioconjugate Chem. 2007, 18, 263-267 published on Dec. 13, 2006.*
Zhang, Bulletin of the American Physical Society, 2007 APS March Meeting, vol. 52, No. 1, Session C1: Poster Session I, Abstract: C1.00034, published Mar. 5, 2007.*
Jiang, Colloids and Surfaces B: Biointerfaces, 36 (2004) 27-33.*
Supp. European Search Report (dated May 31, 2012), European Appl. No. EP 09832610.1.
Int'l Search Report (dated Jul. 27, 2010), PCT/US09/067668.
Written Opinion of ISA (dated Jul. 27, 2010), PCT/US09/067668.

(Continued)

*Primary Examiner* — Robert C Boyle
(74) *Attorney, Agent, or Firm* — Milstein Zhang & Wu LLC

(57) ABSTRACT

The invention relates to polymers, such as aliphatic polyesters, with grafted zwitterions. More particularly, the invention relates to polyester-graft-phosphorylcholine polymers prepared by ring-opening polymerization and click chemistry, compositions and products comprising same, and related methods and uses, for example, in drug delivery.

6 Claims, 11 Drawing Sheets

Synthesis of PC-grafted polyesters: top – δ-valerolactone homopolymer 4; bottom – L-lactide-containing terpolymer 6

(56) References Cited

OTHER PUBLICATIONS

Han et al. "Grafting BSA onto Poly[L-lactide)-co-carbonate] Microspheres by Click Chemistry", Macromolecular Bioscience, vol. 8, No. 7, pp. 638-644 (Jul. 7, 2008).
Cooper et al. "Polyester-graft-phosphorylcholine prepared by ring-opening polymerization and click chemistry", Chemical Communications, No. 7, pp. 815-817 (Dec. 17, 2008).
Parrish et al. "PEG- and peptide-grafted aliphatic polyesters by click chemistry", J. Am. Chem. Soc., vol. 127, No. 20, pp. 7404-7410 (May 25, 2005).
Lewis :Phosphorylcholine-based polymers and their use in the prevention of biofouling, Colloids and Surfaces B. Biointerfaces, vol. 18, No. 3-4, pp. 261-275 (Oct. 1, 2000).

* cited by examiner

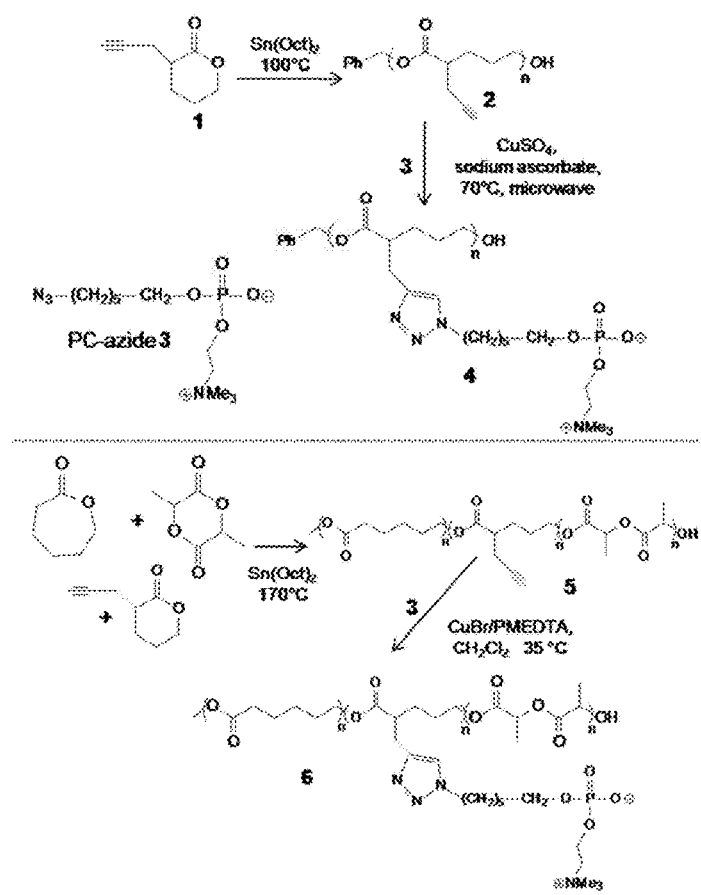
Figure 1. Synthesis of PC-grafted polyesters: top – δ-valerolactone homopolymer 4; bottom – L-lactide-containing terpolymer 6

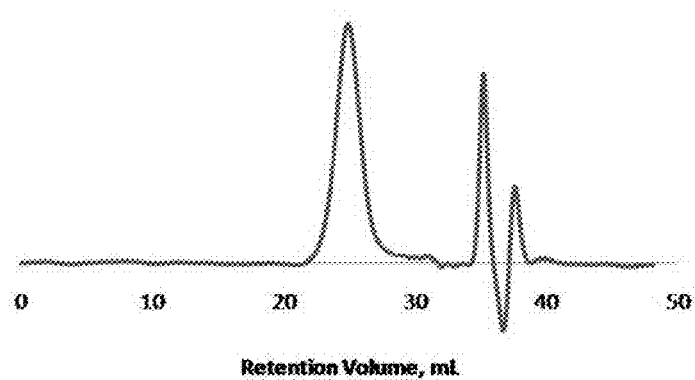
Figure 2. Aqueous GPC trace of PC-grafted polyester (Table 1, entry 2)

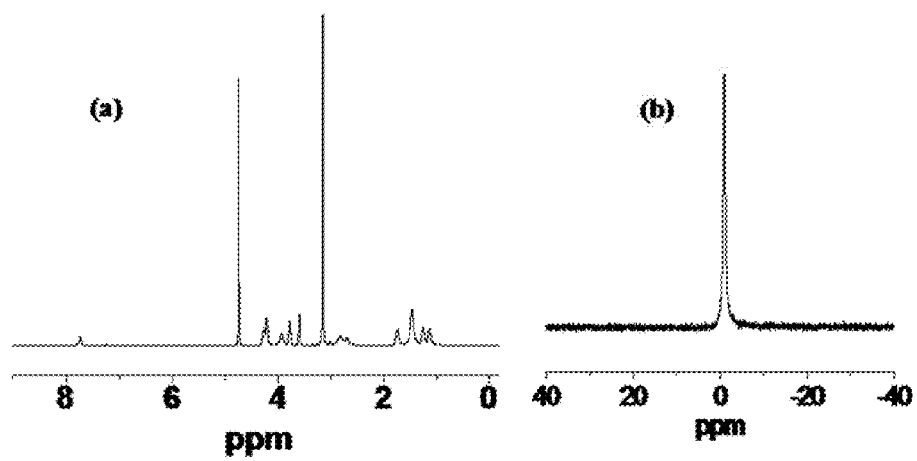
Figure 3. (a) $^1$H and (b) $^{31}$P NMR spectra of polyester-*graft*-PC (Table 1, entry 2).

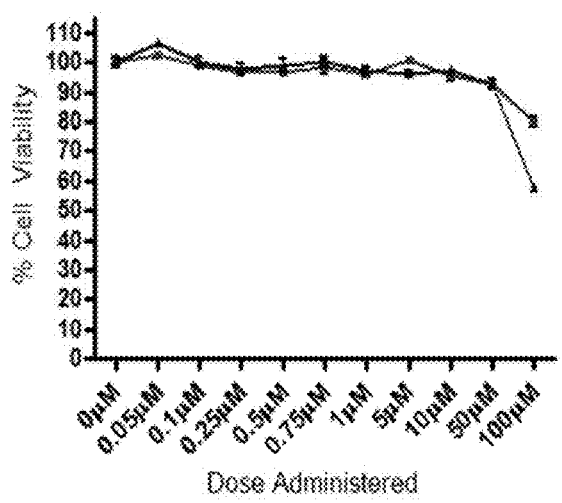
Figure 4. CellTiter-Glow luminescent cell viability assays of PC-*graft*- polyester (Table 1, entry 2) after 24 (red) and 48 hour (blue) incubation in MCF7 cell culture

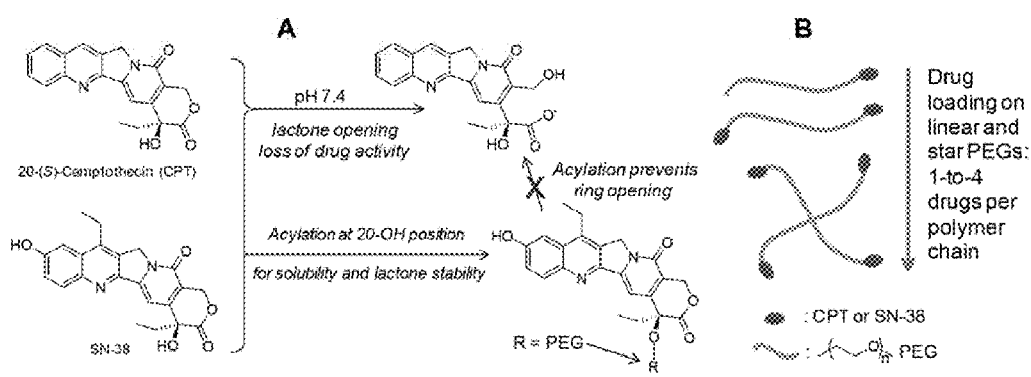
Figure 5. PEGlyation of camptothecin and SN-38 to improve water solubility and structural stability: A) lactone ring stabilization by acylation at the 20-OH position; B) depiction of PEG with chain-end drug substitution.

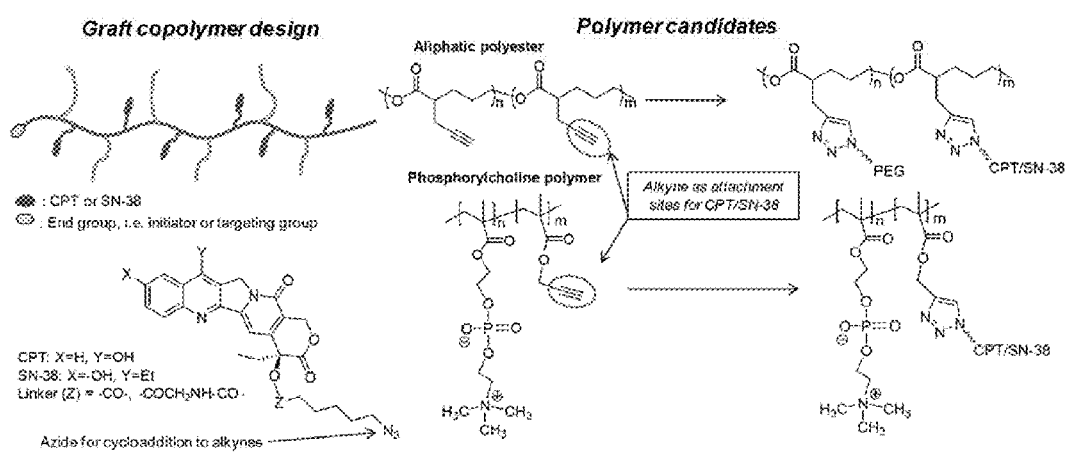
Figure 6. Schematic representation of the proposed highly loaded polymer-drug conjugates.

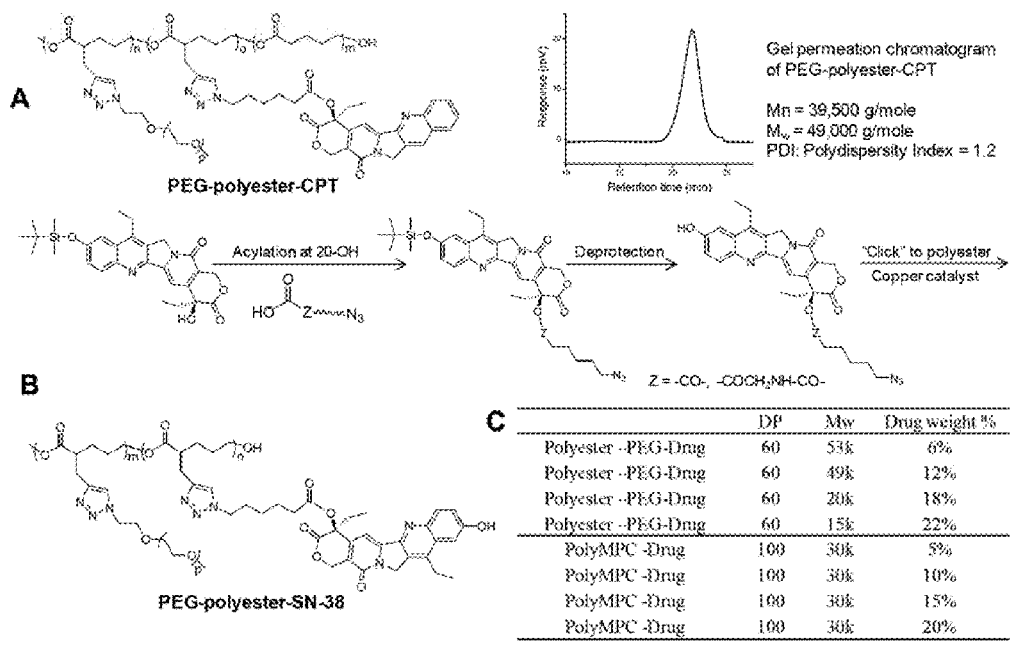

Figure 7. Synthetic routes to graft copolymer drug conjugates. A) structure of PEG-polyester-CPT conjugates prepared to-date; B) synthetic route to PEG-polyester-SN-38 conjugates; C) table showing examples of the proposed aliphatic polyester and polyMPC-drug conjugates to be prepared, including degree of polymerization (DP), molecular weight (Mw), and weight percent drug when the PEG-grafts are 1,100 g/mole.

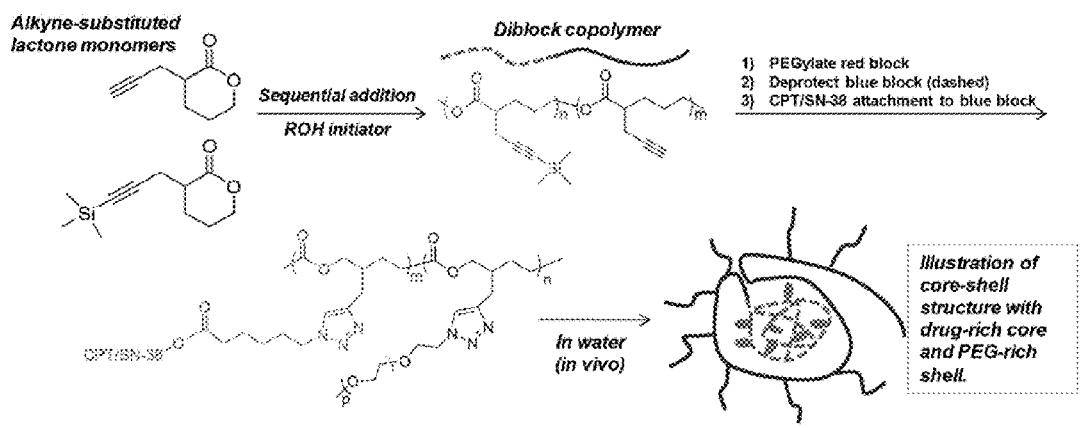
Figure 8. Synthesis of diblock polyester copolymers to give well-defined core-shell structures for drug delivery.

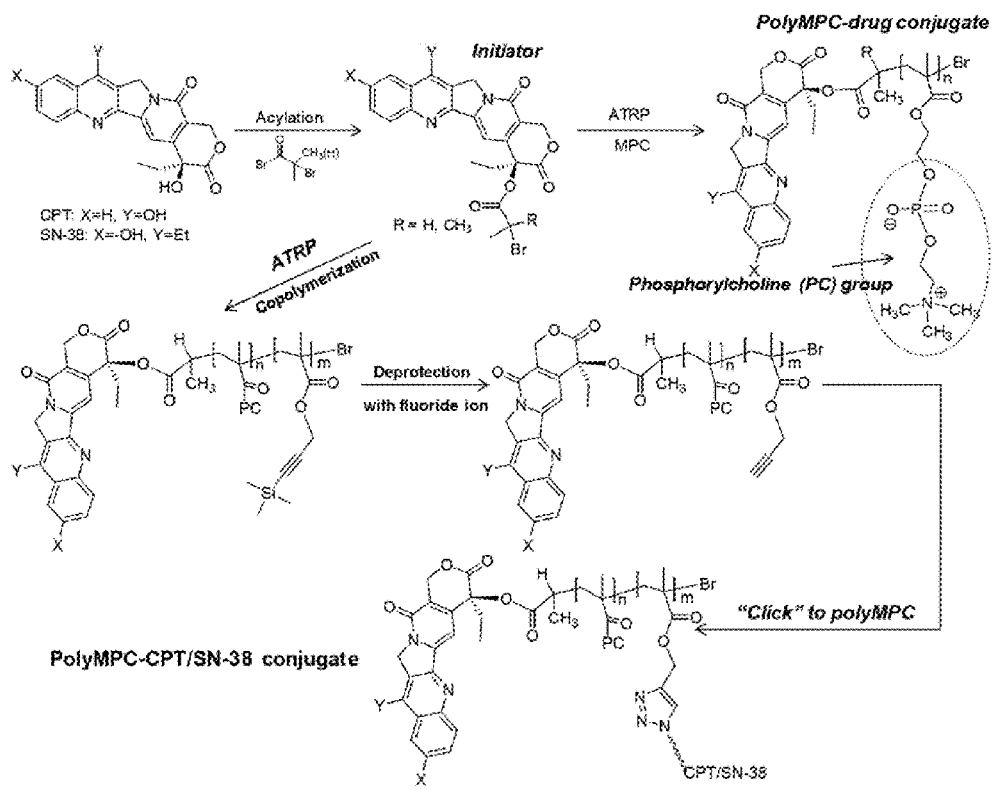
Figure 9. Synthesis of polyMPC-drug conjugates using the drug as an atom transfer radical polymerization (ATRP) initiator and as pendent groups attached by cycloaddition.

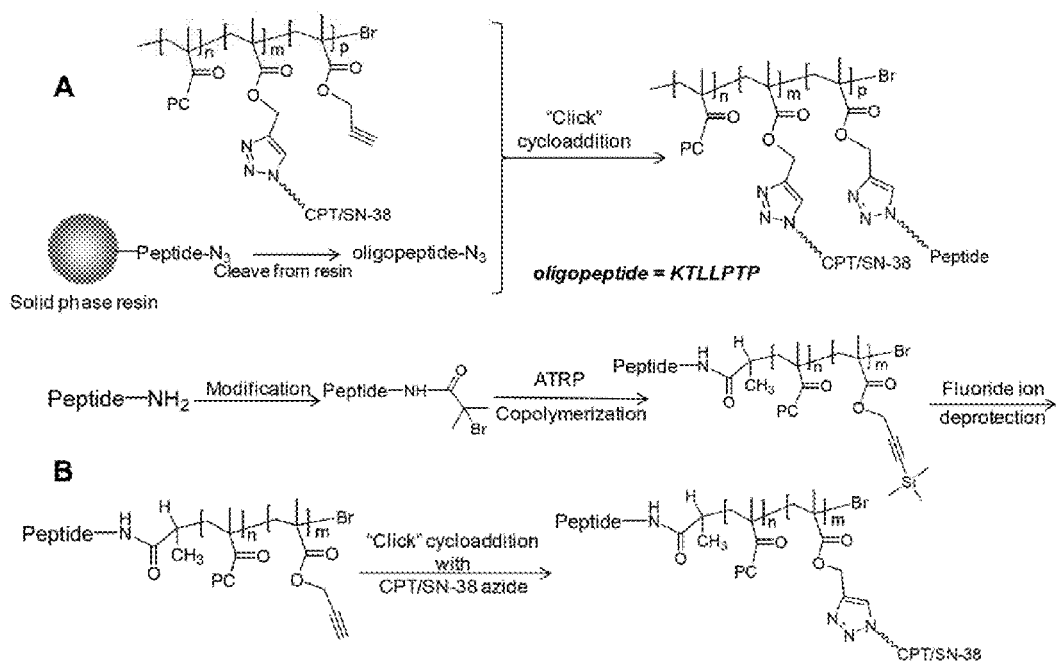
Figure 10. Routes to peptide-targeted polymer-drug conjugates. A) the oligopeptide-azide is attached to the conjugate by cycloaddition with alkyne groups on the polymer; B) the oligopeptide is modified to give an ATRP initiator.

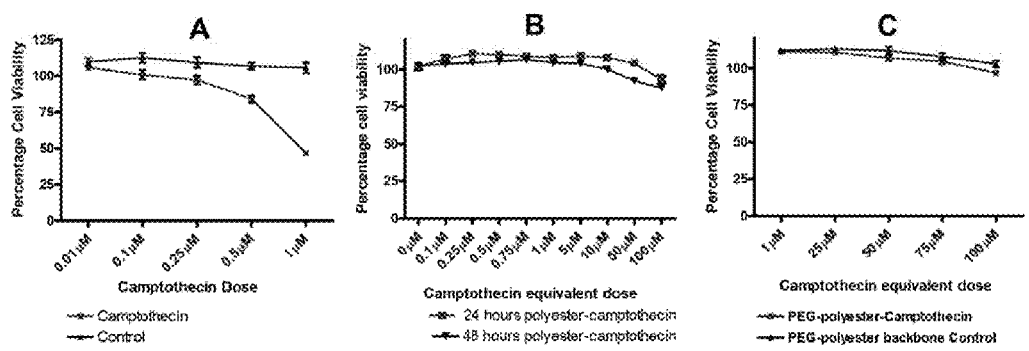

Figure 11. A) 24 hours camptothecin treatment with MCF7 cells induces a dose dependent cytotoxicity; B) 24 and 48 hours incubation of polyMPC-camptothecin with MCF7 cells; C) polyester-camptothecin incubation in cell culture medium followed by 24 hour incubation with MCF7 cells. Percent cell viability data determined by CellTiter-Glo luminescent cell viability assay (Promega) shows that prior to drug release the toxicity of camptothecin is masked by the polymer conjugates (B,C). Errors bars represent ±S.E.M.

POLYESTERS WITH GRAFTED ZWITTERIONS

PRIORITY CLAIMS AND RELATED APPLICATIONS

This application claims the benefit of U.S. Provisional Application Nos. 61/122,065 filed Dec. 12, 2008, and 61/233,982 filed Aug. 14, 2009, the entire content of each of which is expressly incorporated herein by reference.

GOVERNMENT RIGHTS

The United States Government has certain rights to the invention pursuant to Grant No. CBET-0553957 from National Science Foundation to the University of Massachusetts.

FIELD OF THE INVENTION

The invention relates to polymers, such as aliphatic polyesters, with grafted zwitterions. More particularly, the invention relates to polyester-graft-phosphorylcholine polymers prepared by ring-opening polymerization and click chemistry, and compositions and products comprising same, as well as related methods and uses, for example, in drug delivery.

SUMMARY OF THE INVENTION

The invention is based in part on the unexpected discovery of novel polymer-graft-zwitterionic polymers, compositions thereof, and their unique and desirable properties. Such unique polymers, methods for their syntheses, and uses thereof have been discovered to have broad applications such as in the fields of advanced materials and drug delivery.

In one aspect, the invention generally relates to a polymer comprising a monomer subunit having the structure of:

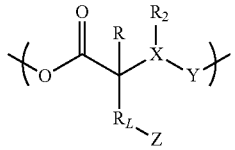

wherein R is hydrogen, an alkyl, halogen, or —$R_L$—Z; $R_L$ is a linking group; X is C or O; Y is a single bond, substituted or unsubstituted —$(CH_2)_a$—, —$(O—CH_2)_b$—, or

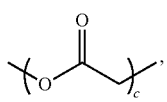

wherein each of a, b or c is independently an integer from about 1 to about 15, e.g., 1, 2, 3, 4, 5, or 6; Z is a group comprising an azide or a carbon-carbon triple bond; and $R_2$ is hydrogen, $(C_1-C_{15})$ alkyl, $(C_1-C_{15})$ alkyloxy, halogen, or absent when X is O. In some embodiments, $R_2$ is hydrogen, $(C_1-C_6)$ alkyl, $(C_1-C_6)$ alkyloxy.

In some embodiments, Z comprises an azide group. In some other embodiment, Z comprises a carbon-carbon triple bond.

In some embodiments, the polymer may further comprise a monomer subunit having the structure:

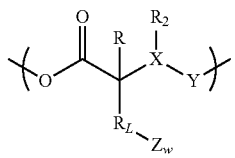

wherein $Z_w$ is a group comprising a zwitterionic moiety. In some embodiments, the zwitterionic moiety comprises one or more of phosphorylcholine and sulfobetaine.

In some embodiments, $Z_w$ comprises a linker group $L_w$ covalently attached to $R_L$ and the zwitterionic moiety

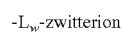

In some embodiments, $L_w$ comprises an alkyl (e.g., $(C_1-C_{15})$ alkyl) or an aryl group (benzyl). In some embodiments, $L_w$ comprises a $(C_1-C_6)$ alkyl.

In some embodiments, the sulfobetaine has the structure:

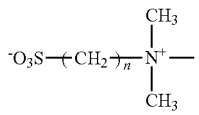

wherein n is 1, 2, 3, 4, 5 or 6.

In some embodiments, $R_L$ is a single bond, or a bivalent $(C_1-C_{15})$ alkyl, $(C_1-C_{15})$ alkyloxy, or $(C_3-C_6)$ aryl group. In some embodiments, $R_L$ is a bivalent $(C_1-C_6)$ alkyl, $(C_1-C_6)$ alkyloxy, or $(C_5-C_6)$ aryl group.

The polymer may further comprise a monomer subunit having the structure:

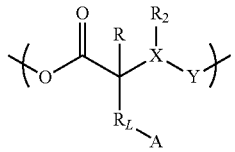

wherein $R_L$ is covalently linked to A (an agent having biological function, e.g., a therapeutic or diagnostic agent).

In another aspect, the invention generally relates to a polymer comprising a monomer subunit having the structure of:

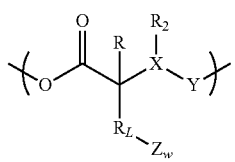

wherein R is hydrogen, an alkyl, halogen, —$R_L$—Z, —$R_L$-A, or —$R_L$—$Z_w$; $R_L$ is a linking group; X is C or O; Y is a single bond, substituted or unsubstituted —$(CH_2)_a$—, —$(O—CH_2)_b$—, or

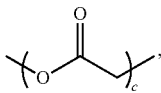

wherein each of a, b or c is independently an integer from about 1 to about 15, e.g., 1, 2, 3, 4, 5, or 6; $R_2$ is hydrogen, $(C_1-C_{15})$ alkyl, $(C_1-C_{15})$ alkyloxy, halogen, or absent when X is O; Z is a group comprising an azide or a carbon-carbon triple bond; A is an agent having a biological activity; and $Z_w$ is a group comprising a zwitterionic moiety. In some embodiments, $R_2$ is hydrogen, $(C_1-C_6)$ alkyl, $(C_1-C_6)$ alkyloxy.

In another aspect, the invention generally relates to a polymer that comprises a monomer subunit having the structure of:

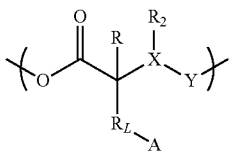

wherein R is hydrogen, an alkyl, halogen, —$R_L$—Z, —$R_L$-A, or —$R_L$—$Z_w$; $R_L$ is a linking group; X is C or O; Y is a single bond, substituted or unsubstituted —$(CH_2)_a$—, —$(O-CH_2)_b$—, or

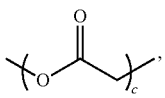

wherein each of a, b or c is independently 1, 2, 3, 4, 5, or 6; $R_2$ is hydrogen, $(C_1-C_6)$ alkyl, $(C_1-C_6)$ alkyloxy, halogen, or absent when X is O; Z is a group comprising an azide or a carbon-carbon triple bond; A is an agent having a biological activity (e.g., a therapeutic or diagnostic agent); and $Z_w$ is a group comprising a zwitterionic moiety.

In yet another aspect, the invention generally relates to a polymer comprising monomer subunits having the structure of:

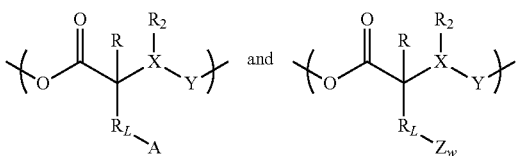

wherein each R is independently hydrogen, an alkyl, halogen, —$R_L$—Z, —$R_L$-A, or —$R_L$—$Z_w$; each $R_L$ is independently a linking group; each X is independently C or O; each Y is independently a single bond, substituted or unsubstituted —$(CH_2)_a$—, —$(O-CH_2)_b$—, or

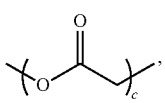

wherein each of a, b and c is independently an integer from about 1 to about 15, e.g., 1, 2, 3, 4, 5, or 6; each $R_2$ is independently hydrogen, $(C_1-C_{15})$ alkyl, $(C_1-C_{15})$ alkyloxy, halogen, or absent when X is O, Z is a group comprising an azide or a carbon-carbon triple bond; A is an agent having a biological activity (an agent having biological function, e.g., a therapeutic or diagnostic agent), and $Z_w$ is a group comprising a zwitterionic moiety. In some embodiments, $R_2$ is hydrogen, $(C_1-C_6)$ alkyl, $(C_1-C_6)$ alkyloxy.

In some embodiments, the agent is a therapeutic agent for treating cancer.

In yet another aspect, the invention generally relates to a polymer comprising a monomer subunit having the structure of:

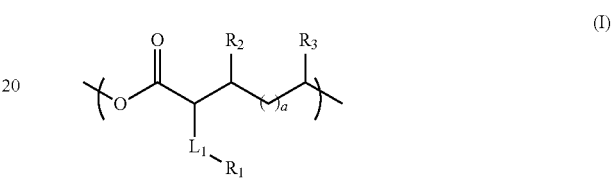

(I)

wherein $L_1$ is a linker group; $R_1$ is a group comprising a zwitterionic moiety; each of $R_2$ and $R_3$ is independently selected from the group consisting of hydrogen, $(C_1-C_{15})$ alkyl, $(C_1-C_{15})$ alkyloxy, halogen, and —OH; and a is 0, 1, 2, 3. In some embodiments, each of $R_2$ and $R_3$ is independently selected from the group consisting of hydrogen, $(C_1-C_6)$ alkyl, $(C_1-C_6)$ alkyloxy.

In some embodiments, the polymer may further comprise a monomer subunit having the structure of:

(II)

wherein $R_4$ is selected from the group consisting of hydrogen, $(C_1-C_{15})$ alkyl, $(C_1-C_{15})$ alkyloxy, and halogen; and b is 0, 1, 2, 3, 4, 5, 6. In some embodiments, $R_4$ is selected from the group consisting of hydrogen, $(C_1-C_6)$ alkyl, $(C_1-C_6)$ alkyloxy.

In some embodiments, the polymer may further comprise a monomer subunit having the structure of:

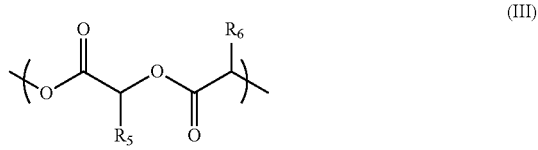

(III)

wherein each of $R_5$ and $R_6$ each is independently selected from the group consisting of hydrogen, $(C_1-C_{15})$ alkyl, $(C_1-C_{15})$ alkyloxy, and halogen. In some embodiments, each of $R_5$ and $R_6$ each is independently selected from the group consisting of hydrogen, $(C_1-C_6)$ alkyl, $(C_1-C_6)$ alkyloxy.

In certain other embodiments, the polymer may comprise one or more of the following monomer subunits:

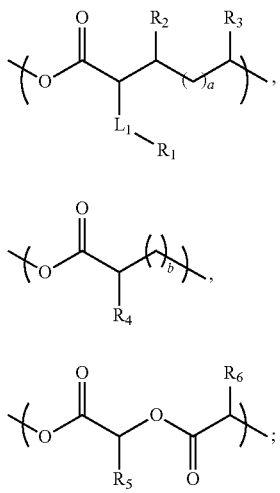

wherein $R_1$ comprises phosphorylcholine; $L_1$ is a —$(CH_2)_n$— group wherein n is an integer from about 1 to about 15, e.g., 1, 2, 3, 4, 5, or 6; each of $R_2$, $R_3$, $R_4$, $R_5$, and $R_6$ is independently selected from the group consisting of hydrogen, ($C_1$-$C_{15}$) alkyl, and halogen; a is 1 or 2; and b is 3 or 4. In certain detailed embodiments, each of $R_2$, $R_3$, $R_4$, $R_5$, and $R_6$ is independently selected from the group consisting of hydrogen, methyl, ethyl, F, and Cl. In some embodiments, each of $R_2$, $R_3$, $R_4$, $R_5$, and $R_6$ is independently selected from the group consisting of hydrogen, ($C_1$-$C_6$) alkyl, and halogen.

In some embodiments, the zwitterionic moiety is phosphorylcholine, and $L_1$ comprises

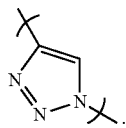

In certain embodiments, the ratios of (I):(II):(III) may be about (10%-60%):(10%-60%):(5%-40%), for example 40%: 40%:20%. The polymer may have $M_w$ from about 8 kDa to about 100 kDa and $M_n$ from about 5 kDa to about 80 kDa.

In another aspect, the invention generally relates to a polymer comprising a monomer subunit having the structure of:

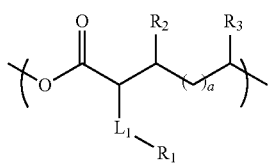

and further comprising at least one of the following monomer subunits:

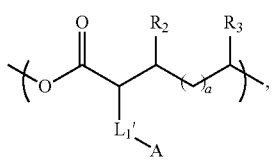

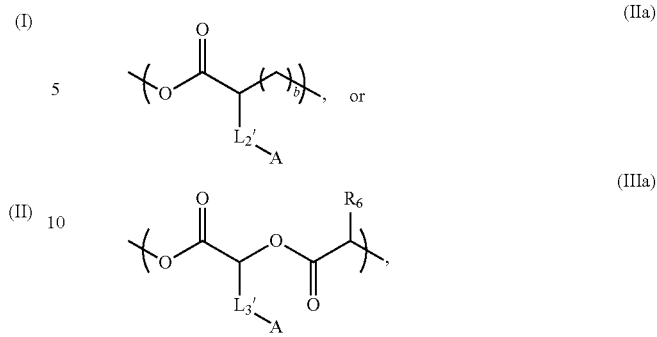

wherein $R_1$ is a group comprising a zwitterionic moiety; each of $R_2$, $R_3$, $R_4$, $R_5$, and $R_6$ is independently selected from the group consisting of hydrogen, ($C_1$-$C_{15}$) alkyl, ($C_1$-$C_{15}$) alkyloxy, halogen, and —OH; a is 0, 1, 2, 3; b is 0, 1, 2, 3, 4, 5, 6; and each of $L_1$, $L_{1'}$, $L_{2'}$ and $L_{3'}$ is independently a linker group linked A (an agent having biological function, e.g., a therapeutic or diagnostic agent). In some embodiments, each of $R_2$, $R_3$, $R_4$, $R_5$, and $R_6$ is independently selected from the group consisting of hydrogen, ($C_1$-$C_6$) alkyl, ($C_1$-$C_6$) alkyloxy, halogen, and —OH.

The agent may be a therapeutic agent or a diagnostic agent such as a biomarker.

In some embodiments, the agent is selected from campothecin, irinotecan, SN-38, doxorubicin, and derivatives thereof.

In some embodiments, the zwitterionic moiety is phosphorylcholine, and at least one of $L_1$, $L_{1'}$, $L_{2'}$ and $L_{3'}$ comprises

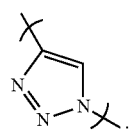

The ratio of zwitterionic moiety:agent may be from about 1:1 to about 20:1, e.g., from about 2:1 to about 10:1, or from about 4:1 to about 8:1. In some embodiments, the ratio of zwitterionic moiety:agent is about 5:1. The polymer may have a $M_w$ from about 8 kDa to about 100 kDa and a $M_n$ from about 5 kDa to about 80 kDa.

In yet another aspect, the invention generally relates to a polyester terpolymer comprising zwitterion-functionalized pedant groups and biological agent-coupled pedant groups. In some embodiments, the zwitterionic moiety may be phosphorylcholine, and the pendant groups comprise

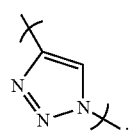

The ratio of zwitterionic moiety:agent may be from about 2:1 to about 10:1, for example, 5:1. The polymer may have a $M_w$ from about 8 kDa to about 100 kDa and a $M_n$ from about 5 kDa to about 80 kDa.

In certain embodiments, the polymer of the invention is cross-linked. Cross-linking can be achieved by any methods known in the art that achieve the desired results.

BRIEF DESCRIPTION OF THE DRAWINGS

FIG. 1 shows an exemplary synthesis of PC-grafted polyesters.

FIG. 2 shows an exemplary aqueous GPC trace of PC-grafted polyester.

FIG. 3 shows an exemplary NMR spectra of an exemplary polyester-graft-PC.

FIG. 4 shows an exemplary CellTiter-Glow luminescent cell viability assays of PC-graft-polyester.

FIG. 5 shows an exemplary PEGylation of camptothecin and SN-38.

FIG. 6 shows a schematic representation of the proposed highly loaded polymer-drug conjugates.

FIG. 7 shows exemplary synthetic routes to graft copolymer drug conjugates.

FIG. 8 shows an exemplary synthesis of diblock polyester copolymers to give well-defined core-shell structures for drug delivery.

FIG. 9 shows an exemplary synthesis of polyMPC-drug conjugates.

FIG. 10 shows exemplary routes to peptide-targeted polymer-drug conjugates.

FIG. 11 shows exemplary data on polyMPC-camptothecin.

DETAILED DESCRIPTION OF THE INVENTION

The polymer-graft-zwitterionic polymers, and compositions thereof, have unique and desirable properties and may be useful in various applications such as in materials and drug delivery.

a. Aliphatic Polyesters with Grafted Zwitterions

Zwitterionic synthetic polymers, such as those containing phosphorylcholine (PC) moieties, exhibit excellent biocompatibility, due largely to their associated water structure and hydrophilicity that limits protein adsorption. Significant efforts have been directed towards the synthesis and application of polymers from 2-methacryloyloxyethyl phosphorylcholine (MPC) for use as bio-implants and medical devices. Aside from these methacrylate-based structures, use of the PC moiety is sparse, especially relative to hydrophilic polymers such as poly(ethylene glycol) (PEG).

In the present invention, PC groups are introduced to aliphatic polyesters, for example, by click cycloaddition of alkyne-substituted polyesters 2 and 5 with PC-azide 3 (FIG. 1). Through this method, properties of the PC groups are embedded within the biodegradable polyester backbone, giving materials with potential applications that benefit from a combination of biodegradability, biocompatibility, and water solubility.

Aliphatic polyesters, such as poly(ε-caprolactone) and poly(lactide), are attractive for biomedical applications due to their biodegradability and low toxicity upon degradation. However, the scope of applications for aliphatic polyesters is limited by their hydrophobicity and narrow range of facile methods for functionalization. While commercially available aliphatic polyesters lack the backbone functionality needed to readily tailor physical properties, reactive functionality can be imparted to aliphatic polyesters by polymerizing functional lactones.

1,3-Huisgen cycloaddition "click" reactions have proven highly suitable for post-polymerization modification of aliphatic polyesters, as the mild conditions associated with click chemistry allow such reactions to be carried out with little-to-no hydrolytic degradation. In addition, microwave-assisted click chemistry shortens reaction times, allowing higher conversion in some cases. Polar molecules, such as azides, efficiently absorb microwave radiation; this coupled with the localized heating associated with microwave leads to higher reaction yields in shorter time-frames.

The combination of PC-moieties with aliphatic polyesters is rare, limited to end-capped poly(ε-caprolactone) and MPC-block-poly(lactide) structures. Here, PC-grafted aliphatic polyesters are synthesized using click chemistry, giving water solubility to the structures by distributing the PC-grafts along the polymer backbone. Homo- and co-polymerization of α-propargyl-δ-valerolactone (1) begins the grafting strategy illustrated in FIG. 1.

Ring-opening polymerization of alkyne 1, with Sn (II) catalysis and benzyl alcohol initiation, gives alkyne-rich polyesters (2) with low polydispersity indices (PDI<1.2) indicative of a controlled chain-growth polymerization. Alkyne-containing terpolyesters were also prepared with L-lactide and ε-caprolactone comonomers, at high temperature (170° C.) to give higher molecular weight random terpolymers (5). These terpolymers had PDI values of about 2, reflective of transesterification events occurring at high temperature. The L-lactide: ε-caprolactone: α-propargyl-δ-valerolactone terpolymer composition was ~3:1:1, judging from integration values in the $^1$H NMR spectrum recorded in $CDCl_3$. Both types of alkyne-containing polyesters were used for grafting PC groups by click cycloaddition of PC-azide 3. Compound 3 was prepared by the reaction of 6-azido-hexanol with 2-chloro-1,3,2-dioxaphospholane (COP), followed by opening the phospholane ring of the product with trimethylamine. Both microwave-assisted and traditional click chemistry were then used to graft the zwitterionic groups onto the aliphatic polyesters to give PC-polyesters 4 and 6.

TABLE 1

Characterization of polyester-graft-PC

| Entry | Polymer Composition (LA:CL:AVL) | Alkyne polyester $M_n^a$ | PDI | Polyester after PC Grafting % PC | $M_n^b$ | $M_w^b$ | PDI |
|---|---|---|---|---|---|---|---|
| 1 | 0:0:100 | 5,600 | 1.12 | 90% | 4,000 | 7,000 | 1.37 |
| 2 | 0:0:100 | 8,300 | 1.16 | 100% | 10,000 | 13,800 | 1.32 |
| 3 | 60:20:20 | 48,000 | 2.19 | 20% | 14,500 | 20,500 | 1.41 |

$^a$THF GPC, polystyrene standards
$^b$Aqueous GPC, PEO standards

Table 1 provides molecular weight data and percent grafting for examples of alkyne-containing starting materials and polyester-graft-PC products. The starting polyester molecular weights ranged from 5,600 to 48,000 g/mol. Entries 1 and 2 are poly(α-propargyl-δ-valerolactone) homopolymers, while entry 3 incorporates 20 mole percent of alkyne 1 with ε-caprolactone and L-lactide.

The polyester homopolymers were functionalized by click cycloaddition reactions performed in a water/tetrahydrofuran mixture with copper sulfate and sodium ascorbate under constant microwave irradiation at 70° C., giving complete grafting in about five minutes. Characteristic of the completed reaction was the disappearance of alkyne protons at 2.0 ppm in the $^1$H NMR spectrum appearance of triazole signals at 7.6 ppm and methyl group signals of the PC-moiety at 3.2 ppm. The purified polyester-graft-PC structures were typically obtained in yields of 60% or greater as off-white powders. Over several weeks, the polyester-graft-PC polymers absorb water and appear waxy. Lyophilization recovers the powder.

The L-lactide containing terpolymers required different click conditions, due to lower solubility of the starting material and the greater hydrolytic lability of the lactide-rich structures. For the terpolymers, the click reactions were performed in dichloromethane with CuBr-PMDETA. The initially homogenous reaction mixture became cloudy over the course of the reaction, as the solubility of the polymer in dichloromethane decreased with increasing PC-substitution. Nonetheless, the PC moiety was found to be incorporated completely into the structure, with isolated polymer yields of nearly 70%. Similar to the homopolymers, the terpolymers were isolated as off-white powders.

The polyester-graft-PC products were purified by treatment with Cuprisorb™ to remove copper, followed by dialysis in water. While the alkyne polyester starting materials 2 and 5 are hydrophobic, and PC azide 3 is amphiphilic, the polyester-graft-PC materials are found to give homogeneous solutions in water only, and are not soluble in most organic solvents. The GPC traces of these polyesters were monomodal, Gaussian curves. For the low molecular weight examples, the relative molecular weights obtained by GPC were in quite reasonable agreement with the expected molecular weights. The higher molecular weight terpolymer with lower grafting density gave a lower than expected molecular weight by GPC, likely due to the effect of having a collapsed structure in water.

FIG. 2 shows the gel permeation chromatogram (refractive index detection) of the polyester-graft-PC with a number average molecular weight ($M_n$) of 10,000 g/mol and PDI of 1.3 based on PEO standards (entry 2 in Table 1; methanol flow marker at ~34 minutes). The relatively low polydispersity index reflects the clean click chemistry possible in these systems. While there are changes in the PDI in the polyester-graft-PC product relative to their respective alkyne-containing starting materials, this is not likely a result of significant degradation; confirmed by the absence of $^1$H-NMR spectrum signals at 4.5 ppm that typify degradation.

FIG. 3 shows the $^1$H and $^{31}$P NMR spectra of a representative polyester-graft-PC sample. In the $^1$H NMR spectrum, the click cycloaddition is confirmed by the appearance of the triazole signal at 7.7 ppm, the PC N-methyls at 3.2 ppm, and the absence of an alkyne proton signal (otherwise appearing at 2.0 ppm). The $^{31}$P NMR spectrum (FIG. 3-B) shows a single resonance corresponding to the attached PC group at −0.4 ppm. This resonance is shifted slightly upfield from that of PC-azide 3.

Finally, the PC-grafted aliphatic polyesters were evaluated for cytotoxicity in cell culture. For example, as shown in FIG. 4, the cell viability assay of the human breast cancer cell line MCF7 (American Type Cell Culture) performed in the presence of PC-grafted polyester showed good cell viability, determined using the CellTiter-Glo luminescent assay (Promega), as expected for these PC-containing macromolecules. With polymer concentrations under 100 $\mu M_W$ very little cell death was found at 24 or 48 hours; cell viability fell off at higher concentrations. The ability to safely use these PC-polyesters at appropriate concentrations will open potential routes for their in vivo applications.

In one aspect, the invention generally relates to a polymer comprising a monomer subunit having the structure of:

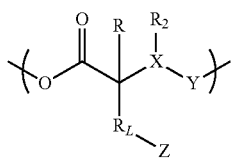

wherein R is hydrogen, an alkyl, halogen, or —$R_L$—Z; $R_L$ is a linking group; X is C or O; Y is a single bond, substituted or unsubstituted —$(CH_2)_a$—, —$(O-CH_2)_b$—, or

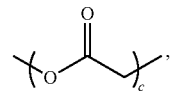

wherein each of a, b or c is independently an integer from about 1 to about 15, e.g., 1, 2, 3, 4, 5, or 6; Z is a group comprising an azide or a carbon-carbon triple bond; and $R_2$ is hydrogen, $(C_1$-$C_{15})$ alkyl, $(C_1$-$C_{15})$ alkyloxy, halogen, or absent when X is O. $R_2$ is hydrogen, $(C_1$-$C_6)$ alkyl, or $(C_1$-$C_6)$ alkyloxy.

In some embodiments, Z comprises an azide group. In some other embodiment, Z comprises a carbon-carbon triple bond.

In some embodiments, the polymer may further comprise a monomer subunit having the structure:

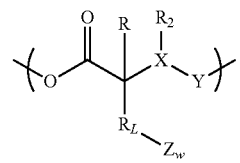

wherein $Z_w$ is a group comprising a zwitterionic moiety. In some embodiments, the zwitterionic moiety comprises one or more of phosphorylcholine and sulfobetaine.

In some embodiments, $Z_w$ comprises a linker group $L_w$ covalently attached to $R_L$ and the zwitterionic moiety

In some embodiments, $L_w$ comprises an alkyl (e.g., $(C_1$-$C_{15})$ alkyl) or a $(C_3$-$C_{10})$ aryl group (e.g., benzyl). In some embodiments, $L_w$ comprises a $(C_1$-$C_6)$ alkyl or a $(C_5$-$C_6)$ aryl group.

For example, 4-azidobenzylphosphorylcholine was made as follows: 4-aminobenzyl alcohol was treated with HCl and reacted with sodium nitrate, followed by sodium azide to yield 4-azidobenzyl alcohol. The product was recovered in 55% yield as a brown solid and purified by column chromatography. The product was characterized by NMR and IR. 4-azidobenzyl alcohol was treated with triethylamine, and 2-chloro-2-oxo-1,3,2-dioxaphospholane (COP) was added to the solution. The resulting compound was reacted with trimethylamine to yield the final product of 4-azidobenzylphosphorylcholine. The final product was obtained as a pale brown powder in 60% yield and characterized by NMR and IR.

In some embodiments, the sulfobetaine has the structure:

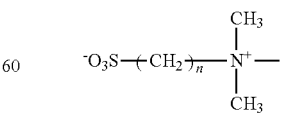

wherein n is an integer from about 1 to about 15, e.g., 1, 2, 3, 4, 5 or 6.

In some embodiments, $R_L$ is a single bond, or a bivalent $(C_1$-$C_{15})$ alkyl, $(C_1$-$C_{15})$ alkyloxy, or $(C_3$-$C_{10})$ aryl group. In some embodiments, $R_L$ is a bivalent $(C_1$-$C_6)$ alkyl, $(C_1$-$C_6)$ alkyloxy, or $(C_5$-$C_6)$ aryl group.

The polymer may further comprise a monomer subunit having the structure:

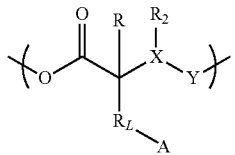

wherein $R_L$ is covalently linked to A (an agent having biological function, e.g., a therapeutic or diagnostic agent).

In another aspect, the invention generally relates to a polymer comprising a monomer subunit having the structure of:

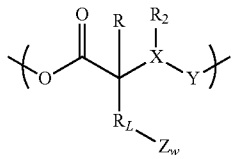

wherein R is hydrogen, an alkyl, halogen, —$R_L$—Z, —$R_L$-A, —$R_L$—$Z_w$; $R_L$ is a linking group; X is C or O; Y is a single bond, substituted or unsubstituted —$(CH_2)_a$—, —$(O$—$CH_2)_b$—, or

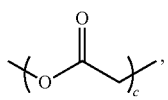

wherein each of a, b or c is independently an integer from about 1 to about 15, e.g., 1, 2, 3, 4, 5, or 6; $R_2$ is hydrogen, $(C_1$-$C_{15})$ alkyl, $(C_1$-$C_{15})$ alkyloxy, halogen, or absent when X is O; Z is a group comprising an azide or a carbon-carbon triple bond; A is an agent having a biological activity (an agent having biological function, e.g., a therapeutic or diagnostic agent); and $Z_w$ is a group comprising a zwitterionic moiety. In some embodiments, $R_2$ is hydrogen, $(C_1$-$C_6)$ alkyl, or $(C_1$-$C_6)$ alkyloxy.

In another aspect, therefore, the invention generally relates to a polymer comprising a monomer having the structure of:

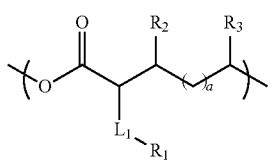

wherein $L_1$ is a linker group; $R_1$ is a group comprising a zwitterionic moiety; each of $R_2$ and $R_3$ is independently selected from the group consisting of hydrogen, $(C_1$-$C_{15})$ alkyl, $(C_1$-$C_{15})$ alkyloxy, halogen, and —OH; and a is 0, 1, 2, 3. In some embodiments, each of $R_2$ and $R_3$ is independently selected from the group consisting of hydrogen, $(C_1$-$C_6)$ alkyl, $(C_1$-$C_6)$ alkyloxy, halogen, and —OH.

In some embodiments, the polymer may further comprise a monomer subunit having the structure of:

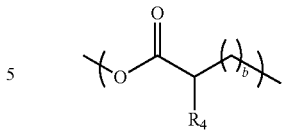

wherein $R_4$ is selected from the group consisting of hydrogen, $(C_1$-$C_{15})$ alkyl, $(C_1$-$C_{15})$ alkyloxy, and halogen; and b is 0, 1, 2, 3, 4, 5, 6. In some embodiments, $R_4$ is selected from the group consisting of hydrogen, $(C_1$-$C_6)$ alkyl, $(C_1$-$C_6)$ alkyloxy, and halogen.

In some embodiments, the polymer may further comprise a monomer subunit having the structure of:

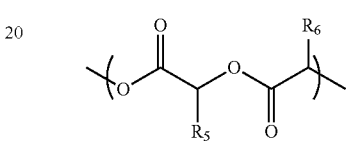

wherein each of $R_5$ and $R_6$ is independently selected from the group consisting of hydrogen, $(C_1$-$C_{15})$ alkyl, $(C_1$-$C_{15})$ alkyloxy, and halogen. In some embodiments, each of $R_5$ and $R_6$ is independently selected from the group consisting of hydrogen, $(C_1$-$C_6)$ alkyl, $(C_1$-$C_6)$ alkyloxy, and halogen.

In certain other embodiments, the polymer may comprise one or more of the following monomer subunits:

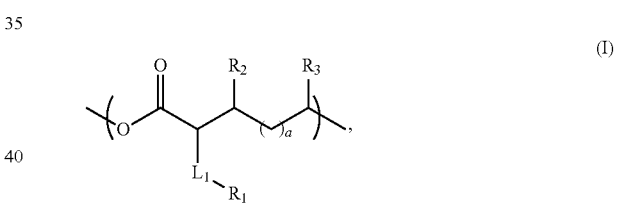

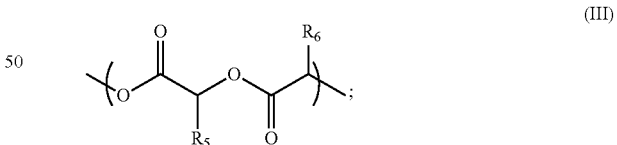

wherein the zwitterionic moiety is phosphorylcholine; $L_1$ is a —$(CH_2)_n$— group wherein n is an integer from about 1 to about 15, e.g., 1, 2, 3, 4, 5, or 6; each of $R_2$, $R_3$, $R_4$, $R_5$, and $R_6$ is independently selected from the group consisting of hydrogen, $(C_1$-$C_{15})$ alkyl, halogen; a is 1 or 2; and b is 3 or 4. In some embodiments, each of $R_2$, $R_3$, $R_4$, $R_5$, and $R_6$ is independently selected from the group consisting of hydrogen, $(C_1$-$C_6)$ alkyl, and halogen. In certain detailed embodiments, each of $R_2$, $R_3$, $R_4$, $R_5$, and $R_6$ is independently selected from the group consisting of hydrogen, methyl, ethyl, F, and Cl.

In some embodiments, the zwitterionic moiety is phosphorylcholine, and $L_1$ comprises

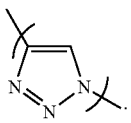

In certain embodiments, the ratios of (I):(II):(III) may be about (10%-60%):(10%-60%):(5%-40%), for example 40%:40%:20%. The polymer may have $M_w$ from about 8 kDa to about 100 kDa and $M_n$ from about 5 kDa to about 80 kDa.

Thus, the invention enables the synthesis and characterization of unique polymers, such as water-soluble, biodegradable, zwitterionic aliphatic polyesters using ring-opening polymerization and post-polymerization click chemistry with PC-azide 3. The phosphorylcholine moiety imparts hydrophilicity to the polyester, and can be viewed as a PEG alternative. The biocompatibility of PC-functionalized aliphatic polyesters suggests their usefulness for integration into medical devices, biomaterials, and drug delivery vehicles.

In certain such embodiments, copolymers (including terpolymers) of the invention can be random or nonrandom. In some embodiments, a polymer is a block copolymer, e.g., di-, tri- or other multi-block copolymers.

b. Polymer Therapeutics

In another aspect, the invention generally relates to polymer therapeutics. More particularly, polymer therapeutics may be synthesized with attachment of drugs used to treat certain conditions, such as pancreatic cancer. For example, biologically active agents such as camptothecin and SN-38, may be attached to synthetic polymer backbones in novel and innovative ways that can simultaneously impart good drug solubility, high loading levels, structural stability, and targeting on a single polymer chain. The invention may be applied to prepare macromolecules having multiple drugs pendent to the polymer backbone, and surround the drugs by other desired groups (i.e., for solubilization and targeting) in well-defined ratios. The high drug loading resulting from this approach is desired for polymer therapeutics, but cannot be achieved by conventional PEGylation methods.

Polymer therapeutics, and specifically the use of polymers as carriers for drugs, has shown promise for improving the efficacy of injectable drugs. While the most clinically advanced polymer therapeutics are polymer-modified protein drugs, delivery of small molecule cancer drugs also stands to benefit from polymer conjugation. PEGylation of cancer drugs, which describes the covalent attachment of poly(ethylene glycol) (PEG) to the drug molecule, improves their water solubility and dramatically increases their effective size. Improving water solubility of cancer drugs is essential for more effective administration and dosing. Increasing the hydrodynamic radius (or effective size during circulation) of cancer drugs leads to their longer circulation lifetime in the bloodstream (i.e., less rapid clearance), preferential uptake into the more open vasculature of cancer tissue relative to healthy tissue, and subsequent retention in the cancer tissue due poor lymphatic drainage. This passive uptake mechanis$M_w$ described as the enhanced permeation and retention (EPR) effect, helps localize chemotherapeutics in cancer tissue, thus limiting deleterious side-effects on healthy tissues. Polymer-functionalized cancer drugs also have advantages of shelf-life and storage (e.g., as dry powders) relative to delivery systems such as liposomal formulations that require solution storage at appropriate concentration and temperature.

As an example, this invention can improve the solubility and drug-loading levels of camptothecin, and camptothecin derivatives such as SN-38, by their covalent attachment to aliphatic polyesters and phosphorylcholine-based polymers. The chosen syntheses provide routes to high drug loading on the polymer backbone, far exceeding reported state-of-the-art polymer-camptothecin drug delivery systems. Evaluation of the toxicity of these conjugates relative to the unmodified drugs, by cell culture assays, will compliment the synthetic work, and provide leads when considering xenograft animal models and biodistribution studies following the proposal period.

One example of cancer that may be treated with the methods of the invention is pancreatic cancer, which is associated with low survival rates chiefly due to high metastatic potential and late presentation at the time of diagnosis. Some therapeutic strategies to control and treat pancreatic cancer include the use of monoclonal antibodies against epidermal growth factor receptors (EGFR) and death receptors, tyrosine kinase inhibitors and chemotherapeutic drugs such as camptothecin. Camptothecin and its derivatives such as SN38 are lipophilic, potent anticancer drugs that induce cell death by inhibiting DNA replication and transcription post topoisomerase I inhibition in rapidly dividing cells. Some reported strategies using PEGylated camptothecin permit incorporation of very few drug molecules per conjugate resulting in low payload and the need for large amounts of injected material for improved treatment outcomes. Polymer-based therapeutics can be designed to increase the drug payload, and to introduce drug cocktails to overcome drug resistance, and also incorporate specialized functionalities such as tissue specific targeting groups. Targeting moieties such as antibodies, small molecules and oligopeptides provide added benefits to therapeutic vehicles by decreasing systemic toxicity and enabling lower dosing for effective treatment. Recently, Kelly, et al. identified a 7 amino acid peptide sequence (KTLLPTP) as a targeting molecule specific for plectin-1 intermediate filament protein, a novel biomarker for pancreatic ductal adenocarcinoma (PDAC) cells. Plectin-1 shows membrane localization in only PDAC cells, in contrast to normal pancreatic ductal cells, conferring an ability to distinguish between cancerous and normal pancreatic cells. In vivo experiments in mice using the heptapeptide directed against plectin-1 confirmed high pancreatic tumor tissue specificity and uptake as compared to normal tissue uptake. Thus, this peptide sequence represents a suitable candidate for use as a targeting signal for the polymer-camptothecin/SN38 conjugates described in this proposal.

Two problems with camptothecin and its derivatives, specifically poor water solubility and structural instability, must be addressed to optimize their use in cancer treatment, and to reduce serious side-effects, such as life-threatening dehydration, associated with their use. Polymers are well-suited for improving water solubility, especially through conjugation methods using biocompatible, water soluble polymers such as poly(ethylene glycol) (PEG) and phosphorylcholine-based structures. As illustrated in FIG. 5, the lactone ring of camptothecin is susceptible to ring-opening under physiological conditions, and the ring-opened form is completely inactive against tumor cells. Camptothecin derivatives such as SN-38 (hydroxyl group at the 10 position) carry identical problems. Stabilization of the lactone ring of camptothecin derivatives is best accomplished by acylation (ester formation) at the 20-OH position. When acylation is performed with carboxylic acid terminated PEG, a polymer-drug conjugate is obtained that is more soluble, and more stable, than the drug alone. Conjugates of this type, containing one, two, or four camptothecin molecules per polymer chain, are also shown in FIG. 5. While this chain-end functionalization approach represents state-of-the-art polymer therapeutics for camptothecin derivatives, it cannot address the high drug loading, or targeting, desired in an optimized polymer-drug molecule.

In one embodiment of the invention, camptothecin and SN-38 are applied to polymer therapeutics in novel and innovative ways that can simultaneously impart drug solubility, loading, stability, and targeting to a single polymer chain. FIG. 6 illustrates the approach of having multiple drugs pendent to a polymer chain, which also contains the other desired groups in well-defined ratios. An azide-modified acylated camptothecin is prepared, and cycloaddition ("click") chemistry is used for its attachment to alkyne-containing polymers. The percentage of alkyne-containing monomer in the polymer structure thus dictates camptothecin loading on the polymer. Upon hydrolysis or enzymolysis, camptothecin cleaves from the backbone in its active lactone form. The principles of polymer therapeutics are expected to localize the drug in the pancreatic tumor area prior to drug cleavage from the backbone.

The present invention thus enables the preparation of novel highly tailored polymer-drug structures as alternatives to current options in chemotherapy. To this end, the synthetic approach is designed to provide unique structures differentiated from those available commercially, or reported in the literature, but sufficiently simple to envisage scale-up to a production level.

Therefore, as an example, the invention relates to the preparation of novel camptothecin-polymer conjugates in which the polymers are biocompatible and water soluble, including a) aliphatic polyesters with grafted poly(ethylene glycol), and b) methacryloyloxyethyl phosphorylcholine (MPC)-based polymers. Syntheses focus on 1) drug payload, by maximizing the number of drugs per polymer chain while maintaining water solubility; 2) linkage chemistries between the drug and the polymer chain; 3) diblock copolymer structures that enable efficient drug encapsulation; and 4) the feasibility of dual functionalization of the polymer with a targeting group.

The invention is also directed at characterizing camptothecin- and SN-38-polymer conjugates in the presence of pancreatic cancer cell lines. Cell culture is performed to determine polymer-campothecin/SN38 drug release dynamics as a function of time and pH, as well as the resulting cytotoxicity arising following drug release. Targeting specificity and efficacy of plectin-1 directed polymer-camptothecin/SN38 conjugates is determined by in vitro settings.

EXAMPLES

This example describes the synthetic chemistry for polymer-camptothecin and polymer-SN-38 preparation, followed by cytotoxicity evaluation in cell culture.

Design 1: Synthesis of Polymer-Camptothecin and Polymer-SN-38 Conjugates.

Polyester-camptothecin conjugates. New, functional lactone monomers are prepared that, upon ring-opening polymerization, give functional aliphatic polyesters. One versatile polyester that has been prepared is the alkyne-substituted version shown in FIG. 7. Functionalization of these alkyne-containing polyesters can be achieved in excellent yield by Huisgen cycloaddition with any of a variety of azide-containing molecules. Successful linking of PEG, cell-adhesion peptide sequences (i.e., RGD), and camptothecin to aliphatic polyesters using azide-functionalized PEG, RGD, and camptothecin have been demonstrated. For camptothecin, the 20-OH position has been acylated with 6-bromohexanoic acid, converting the bromide to an azide, and attaching the drug to the polyester by cycloaddition. Ultimately, in vivo cleavage of the drug-polymer linkage will liberate the native (unmodified) drug with its potent toxicity.

The first synthetic objective is to apply the chemistry that was demonstrated for camptothecin (the natural extract from the tree bark of *camplotheca acuminata*) to SN-38, a semi-synthetic derivative containing a phenol at the 10-position. This requires using a protection/deprotection step of the phenol, which will proceed in straightforward fashion. It is important to adapt similar chemistry to SN-38, as it shows increased cytotoxicity relative to camptothecin itself. Moreover, polymer-based SN-38 prodrugs provide a means to potentially replace irinotecan (i.e., CPT-11), used today as the SN-38 prodrug, which elicits severe side-effects due largely to the bis-piperidinyl by-product of its hydrolysis. The synthetic chemistry for using SN-38 in polyester cycloaddition chemistry is also outlined in FIG. 7.

In the scope of this project, an additional aliphatic polyester is prepared, in order to utilize well-defined solution micellization of block copolymers for pancreatic chemotherapy. FIG. 8 outlines a synthesis of A-B diblock aliphatic polyesters, in which one block contains PEG, or zwitterions such as PC and the other block contains camptothecin or SN-38. In water (or the bloodstream) unimolecular core-corona micelles will form with the more hydrophilic PEG-(or zwitterionic-) rich block as the corona, and the more hydrophobic drug-rich block as the core. Such a structure may be ideal for efficiently encapsulating the drug prior to preferential uptake into tumor tissue (by the EPR effect), after which polyester degradation enables drug release into the tumor. This polyester block copolymer synthesis relies on the sequential polymerization of a trimethylsilyl-protected alkyne lactone and an unprotected alkyne-lactone. A cycloaddition-deprotection-cycloaddition reaction series, as outlined in FIG. 8, completes the desired diblock copolymer synthesis. This series of polymer-drug conjugates vary the following parameters: 1) overall polymer molecular weight, from 10 to 50 kDa; 2) relative length of the two blocks, from 20-80 mole percent drug, in 10% increments; and 3) PEG graft length, from 300-2,200 g/mole, which functions to vary PEG weight percent. This series of conjugates demonstrates the potential advantage of the graft copolymer approach, as they contain a much higher weight percent drug, from about 5% to about 20% or greater, relative to linear Prothecan (i.e., CPT-PEG-CPT) (1.7 wt. %) and star-PEG EZN-2208 (3.7 wt. %) from Enzon, Inc.

MPC-camptothecin and MPC-SN-38 conjugates. A second synthetic thrust centers on conjugating methacryloyloxyethyl phosphorylcholine (MPC) polymers to camptothecin and SN-38. MPC polymers are highly water soluble due to their polyzwitterionic structure. In similar fashion to PEG, MPC polymers carry an associated water structure that masks them from the body's immune response. To date, the commercial availability of end-functional PEGs has led to their widespread use in polymer therapeutics. However, recent discoveries in controlled free radical polymerization, specifically atom transfer radical polymerization, open new opportunities for using MPC polymers in cancer therapeutics. Below is described an approach to functionalize camptothecin and SN-38 with MPC polymers, using the cancer drugs as 1) the polymerization initiator, and 2) as pendent groups along the MPC polymer backbone.

Camptothecin/SN-38 initiators. FIG. 9 depicts the acylation at the 20-OH position of CPT and SN-38 with 2-bromoisobutyryl bromide or 2-bromopropionyl bromide to give atom transfer radical polymerization (ATRP) initiators for polymerizing MPC. These compounds are suitable initiators for ATRP of MPC, a controlled free radical polymerization that leads to MPC-drug conjugates with low polydispersity, a desirable feature for making well-defined macromolecules that can be considered as injectables for drug delivery. Characterization of MPC-drug conjugates by aqueous gel permeation chromatography (GPC) shows them to be the product of a well controlled polymerization, in which molecular weights from 5-25 kDa and PDI values of ~1.2 are obtained. Proton NMR spectroscopy of the conjugates indicate the formation of encapsulated drug, by near baseline broadening of the hydrophobic drug peaks in aqueous solvent, and the appearance of the peaks in polar organic solvents. Critical micelle concentrations of these and other conjugates will be measured by solution light scattering.

MPC with pendant CPT/SN-38. While the use of CPT or SN38 to initiate MPC polymerization will provide the first examples of MPC-camptothecin/SN-38 conjugates for analysis, these conjugates are restricted to one drug per chain; ultimately higher drug loading is desired. PolyMPC-drug conjugates can be synthesized to afford high drug loadings, by copolymerization of MPC and trimethylsilyl (TMS)-protected propargyl methacrylate from a suitable ATRP initiator (either a conventional initiator or a targeting group derivative). This synthesis is also shown in FIG. 9 (bottom). Following the MPC-alkyne methacrylate copolymerization, the TMS groups will be removed with tetra-n-butylammonium fluoride, and the liberated alkynes will be conjugated to camptothecin/SN-38 azide. The ratio of comonomers used in the initial polymerization will dictate the extent of alkyne available for reaction with the azide-labeled drugs.

Polymer-drug conjugates with targeting groups. As the plectin-1 directed peptide (KTLLPTP) has been seen to have specificity for pancreatic cancer tissue in both in vivo and in cell culture experiments, this heptapeptide represents a suitable candidate for use as a targeting molecule for the polymer-camptothecin/SN38 conjugates. The targeting heptapeptide will be introduced into the polymer-drug conjugate by one or both of the pathways shown in FIG. 10. In one approach, the peptide is transformed to an initiator by reacting its amine group with 2-bromoisobutyric acid. The polymer-drug conjugate is then prepared by growing polyMPC from the targeting group initiator. Through variation of alkyne-density in the PC polymer structure, the relative ratio of targeting group per polymer chain can be varied. In these structures, PEG attachment is not needed as the PC-group itself provides the desired water solubility. In a second approach, the targeting group is introduced to the conjugate by click cycloaddition. The peptide-azide, prepared by solid phase peptide synthesis (SPPS), is cleaved from the resin, then reacted with the alkyne-containing polymer.

Drug release measurements. Polymer therapeutic strategies rely on the EPR effect for passive tumor localization; however their success depends heavily on the efficient release of the drugs from the polymer backbones in the tumor microenvironment and in the cells. Tumors, including pancreatic tumors, harbor an acidic environment (~pH 6.0), necessitating design of pH sensitive polymer-drug conjugates. This reasoning is further supported by the fact that most polymer-drug conjugates post cellular entry get trafficked along the endosomal-lysosomal pathway wherein they are exposed to pH 6.5-5.0 in the early and late endosomes to even more acidic regions in the lysosomes.

Time dependent stability of polymer-camptothecin/SN38 conjugates is determined in phosphate buffered saline (PBS), as well as in serum-containing and serum-free cell culture media at different time points. The effect of serum proteins including various esterases on the polymer-drug conjugate stability at physiological pH of 7.4 can then be compared to that in serum-free cell culture medium and in PBS. The Waters Alliance HPLC system connected with a C18 reverse-phase column (250×4.6 mm) is used. Under gradient system of 5-95% acetonitrile in 20 min at a flow rate of 1 mL/min, open-ring and closed-ring camptothecins are well-separated, eluted at retention times of 8.0 and 10.6 min, respectively. The conjugates is dissolved into PBS with different pH values such as pH 7.4 and pH 5.5 to mimic physiological as well as endosomal/lysosomal pH at 37° C. Aliquots is removed at different time intervals, and after addition of an equal amount of dimethyl sulfoxide to dissolve the free drug released from the polymer, the samples is analyzed by HPLC, measuring the drug concentration released from conjugate. The percentage of drug released is calculated on the basis of peak area of the sample at different time points.

Similarly, the polyMPC-drug conjugate is incubated with cell culture media and mouse serum/plasma at 37° C. at different time intervals, then quenched with a 1:1 mixture of acetonitrile/methanol. After vortexing and passage through a 0.2 μm filter membrane, the samples will be analyzed by HPLC.

Drug Release Data of Camptothecin from Random and Diblock PC-Polyester Conjugates.

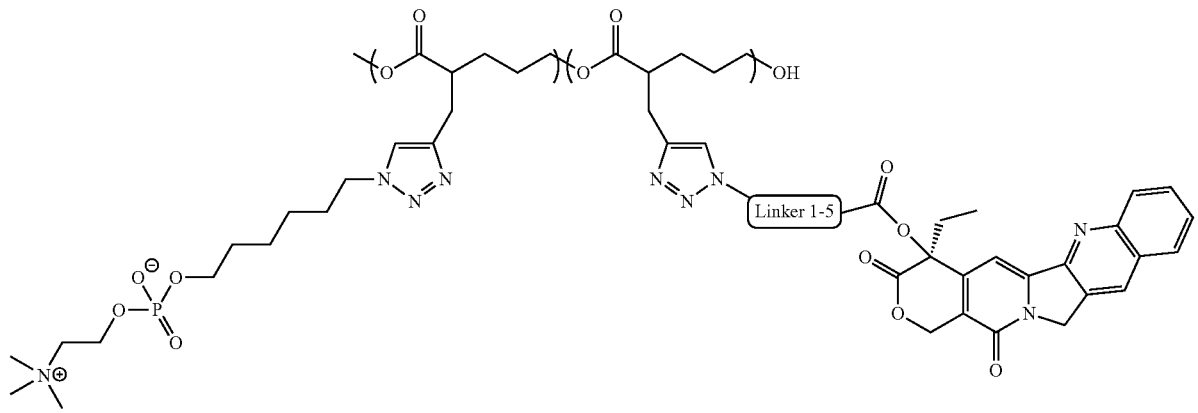

TABLE 2

Half-lives of CPT release from PC-polyester-CPT diblock copolymers with linker 2.

| | | | | | Half life (hours) | | |
|---|---|---|---|---|---|---|---|
| Wt % CPT | Mw | PDI | Wt % PC | PBS | Cell Culture media | Human Plasma | |
| 10 | 46,287 | 1.08 | 80 | 52 | 31 | 9 | |
| 18 | 48,367 | 1.04 | 65 | 49 | 28 | 8 | |
| 30 | 51,642 | 1.02 | 40 | 35 | 12 | 5 | |
| 35 | 69,487 | 1.08 | 30 | 18 | 8 | 2 | |

TABLE 3

Half-lives of CPT release from PC-polyester-CPT random copolymers with linkers 2, 3, 4, and 5.

| | | | | | Half life (hours) | | |
|---|---|---|---|---|---|---|---|
| Wt % CPT | Mw | PDI | Linker | PBS | Cell Culture media | Mouse Serum | Human Plasma |
| 32 | 37,000 | 1.12 | 3 | 18 | 10 | 22 | 2 |
| 25 | 41,000 | 1.14 | 2 | 26 | 16 | 21 | 3 |
| 18 | 43,000 | 1.14 | 4 | 16 | 11 | 13 | 5 |
| 20 | 46,000 | 1.12 | 5 | >168 | >168 | >168 | >168 |

Diblock and random copolymers of functionalized polyesters with pendant functionalities of camptothecin with phosphorylcholine (PC) or poly(ethylene glycol) (PEG) were prepared using click cycloaddition to alkyne-functionalized aliphatic polyesters. Conjugation of the water-insoluble camptothecin to the water-soluble polymers allows for increased loading of camptothecin and the potential for more favorable therapeutic indices due to the enhanced permeation and retention effect. Conjugates based on a random copolymer strategy with PC as the water-solubilizing functionality were analyzed by HPLC to examine the release of camptothecin from the polyester backbone by the different ester linkages. The different linkages are shown below. Exemplary synthetic approach is shown in Scheme 1.

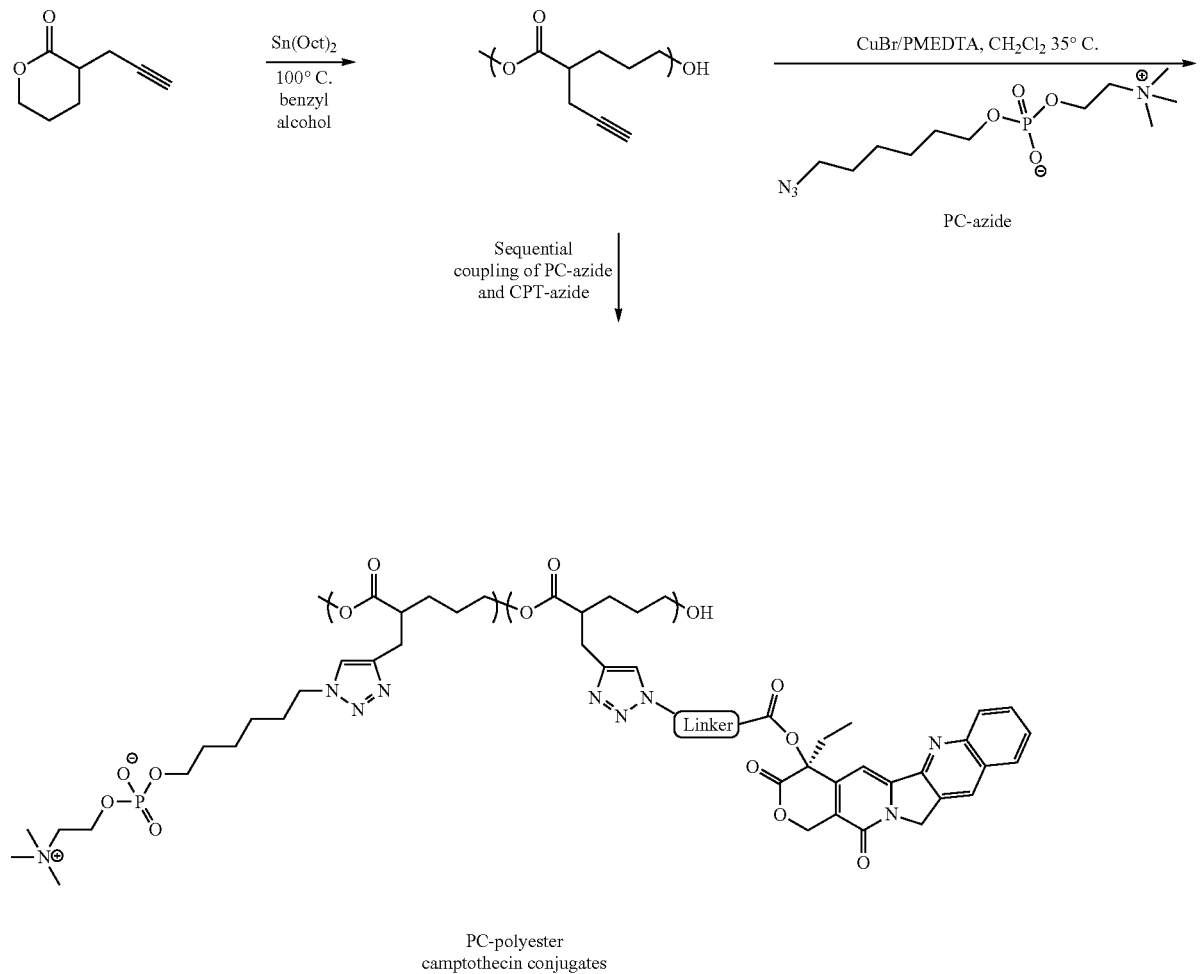

PC-polyester camptothecin conjugates

-continued

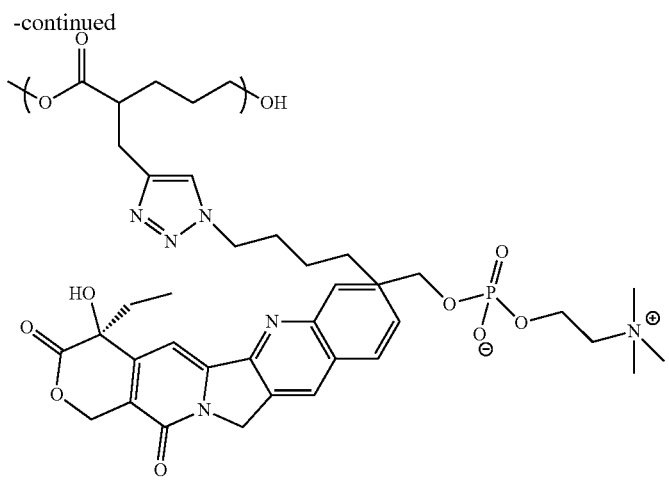

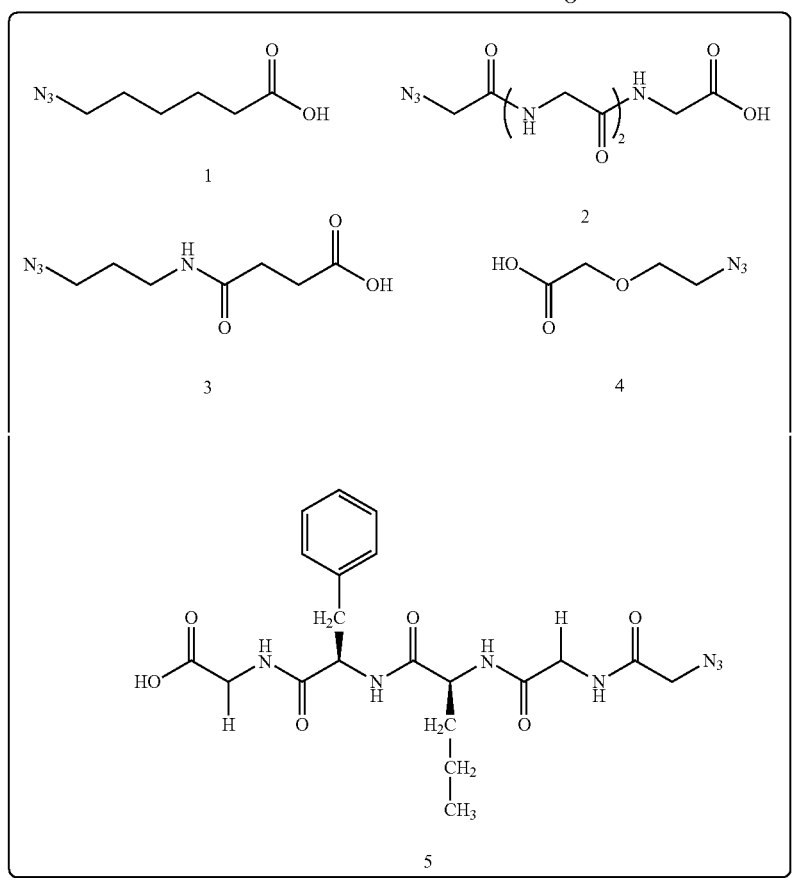

The polyester conjugates were incubated in various media (PBS, cell culture media, mouse seruM_w, human plasma) for up to 1 week. At specific time points, samples were removed and proteins were precipitated by the addition of acetonitrile. After filtration, the samples were analyzed by HPLC with 10% ethanol in PBS as the eluent using a size exclusion column. Based on the areas under the polyester peak and the camptothecin peak (the camptothecin peak increasing over time) the corresponding half-lives were calculated.

From the release of camptothecin, it appears that the PC functionalized diblock polyester conjugates provide the best protection of the camptothecin, as this resulted in the slowest release of the drug, or the longest half-life, when compared with similar amounts of camptothecin in random copolymer PC-based structures, or in PEgylated CPT containing structures. This suggests that the PC-containing diblock copolymers form micelles in solution that provide a measure of control over drug release, a needed feature for in vivo settings.

Design 2: Cell Culture Studies of Polymer-Camptothecin/SN-38 Conjugates.

Cytotoxicity of polymer-camptothecin/SN-38 conjugates. Preliminary cell-culture experiments were conducted using polyMPC-drug conjugates and PEGylated-polyester-drug conjugates, using weight percent camptothecin on human breast adenocarcinoma cells (MCF7) (American Type Culture Collection, ATCC). Unlike the free drugs, the conjugates do not cause any significant cytotoxicity to these cells (FIGS. 11-B and C). This not only demonstrates the biocompatible nature of the polyMPC and PEGylated polyester structures, but also shows that covalent conjugation of the drug to the polymer can mask drug toxicity before its release. Following successful identification of polymer-drug candidates from the hydrolysis studies (see above), cell culture assays will be used to further characterize the conjugates. The human pancreatic cancer cells lines BxPC-3, AsPC-1 (both from ATCC) will be cultured in RPMI-1640 medium supplemented with 10% fetal bovine serum (FBS) and human pancreatic cancer cell line MIA PaCa-2 (ATCC) will be cultured in Dulbecco's modified eagle's medium (DMEM) supplemented with 10% FBS and 2.5% horse seruM$_w$ then incubated at 37° C. At about 70% confluency the cells will be incubated for 24, 48 and 72 hours with varying drug-equivalent concentrations. This provides valuable data associated with 1) stability of the polymer-drug conjugates as a function of time and 2) the pH-sensitivity of camptothecin/SN38 release. Cell viability post treatment is measured using CellTiter-Glo luminescent cell viability assay (Promega) on a FLUOstar OPTIMA plate reader (BMG LABTECH). The percentage camptothecin or SN38-mediated toxicity is then calculated with respect to untreated cells used as a control sample.

Characterization of targeting peptide-polymer-camptothecin/SN38 conjugates. Following successful screening outcomes from the above experiments, polymer-drug conjugates containing the plectin-1 targeting MPC group are synthesized, and their targeting specificity in cell culture characterized. Human pancreatic cancer cells MIA PaCa-2, mouse PDAC and both human and mouse normal pancreatic ductal cells will be incubated for about 1 hour at 37° C. with polymer-drug conjugates, both with and without the plectin-1 heptapeptide. Following cell incubation with polymer conjugates, cells are collected and lysed and the cellular proteins fractionated on a protein gel followed by Western blot analysis. Immunoprobing with plectin-1 antibody (Abcam) will elucidate Plectin-1-polymer interactions recognized by altered plectin-1 molecular weights. Densitometric analysis of the protein bands quantifies the specificity and uptake of polymer conjugates across cancerous and normal pancreatic cells.

Uses for Treating Pancreatic Cancer

The design and methods herein are highly relevant to pancreatic cancer therapy, given the recent strides made with camptothecin derivatives towards this disease. The ability to tailor polymer structures with high drug loading, water solubility, well-defined solution structures and tissue specific peptides for targeted drug delivery enables design of novel and access of polymer therapeutics for treating pancreatic cancer. The polymer therapeutics approach herein shown have several salient features, including: 1) a large drug payload thereby reducing the therapeutic dose administered to the patient and uptake by both the EPR effect and targeted delivery strategies for pancreatic cancer cells, 2) the use of biodegradable or biologically inert polymers for the drug conjugation, which can mask the drug during circulation; 3) a built-in ability to release the attached drug specifically in the tumor microenvironment, and also intra-cellularly. The results will help guide future in vivo work in suitable xenograft pancreatic cancer mice models, for examples, experiments on pharmacokinetic analysis and histology to determine the stability, drug release profiles, specificity and effect of these novel polymer-drug conjugates on pancreatic cancer.

Thus, in another aspect, the polymer of the invention comprises a monomer subunit having the structure of:

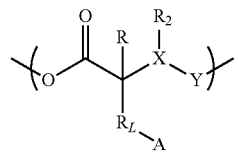

wherein R is hydrogen, an alkyl, halogen, —$R_L$—Z, —$R_L$-A, or —$R_L$—$Z_w$; $R_L$ is a linking group; X is C or O; Y is a single bond, substituted or unsubstituted —$(CH_2)_a$—, —(O—$CH_2)_b$—, or

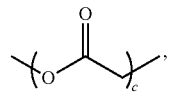

wherein each of a, b or c is independently 1, 2, 3, 4, 5, or 6; $R_2$ is hydrogen, ($C_1$-$C_6$) alkyl, ($C_1$-$C_6$) alkyloxy, halogen, or absent when X is O; Z is a group comprising an azide or a carbon-carbon triple bond; A is an agent having a biological activity (e.g., a therapeutic or diagnostic agent); and Z is a group comprising a zwitterionic moiety.

In another aspect, the invention generally related to a polymer comprising monomer subunits having the structure of:

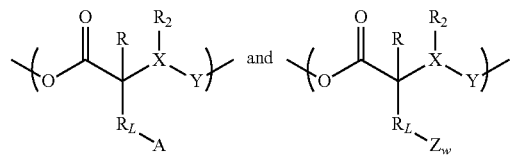

wherein each R is independently hydrogen, an alkyl, halogen, —$R_L$—Z, —$R_L$-A, or —R—$Z_w$; each $R_L$ is independently a linking group; each X is independently C or O; each Y is independently a single bond, substituted or unsubstituted —$(CH_2)_a$-, —(O—$CH_2)_b$—, or

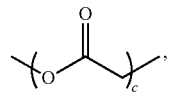

wherein each of a, b and c is independently an integer from about 1 to about 15, e.g., 1, 2, 3, 4, 5, or 6; each $R_2$ is independently hydrogen, ($C_1$-$C_{15}$) alkyl, ($C_1$-$C_{15}$) alkyloxy, halogen, or absent when X is O; each Z is a group comprising an azide or a carbon-carbon triple bond; each A is an agent having a biological activity (an agent having biological function, e.g., a therapeutic or diagnostic agent), or each $Z_w$ is a group comprising a zwitterionic moiety. In some embodiments, each $R_2$ is independently hydrogen, ($C_1$-$C_6$) alkyl, ($C_1$-$C_6$) alkyloxy, and halogen. In some embodiments, the agent is a therapeutic agent for treating cancer.

In yet another aspect, the invention generally relates to a polymer comprising a monomer subunit having the structure of:

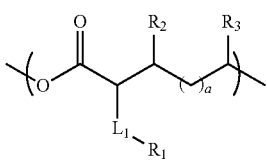

and further comprising at least one of the following monomer subunits:

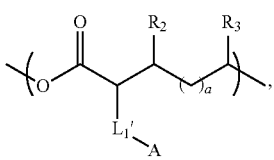

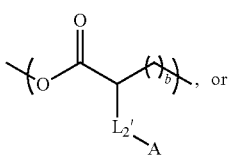

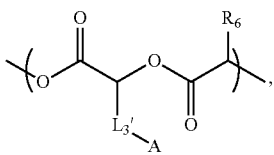

wherein $R_1$ is a group comprising a zwitterionic moiety; each of $R_2$, $R_3$, $R_4$, $R_5$, and $R_6$ is independently selected from the group consisting of hydrogen, ($C_1$-$C_{15}$) alkyl, ($C_1$-$C_{15}$) alkyloxy, halogen, and —OH; a is 0, 1, 2, 3; h is 0, 1, 2, 3, 4, 5, 6; and each of $L_1$, $L_{1'}$, $L_{2'}$ and $L_{3'}$ is independently a linker group linked A (an agent having biological function, e.g., a therapeutic or diagnostic agent). In some embodiments, each of $R_2$, $R_3$, $R_4$, $R_5$, and $R_6$ is independently selected from the group consisting of hydrogen, ($C_1$-$C_6$) alkyl, ($C_1$-$C_6$) alkyloxy, halogen, and —OH.

The agent may be a therapeutic agent or a diagnostic agent such as a biomarker.

In some embodiments, the agent is selected from campothecin, irinotecan, SN-38, doxorubicin, and derivatives thereof.

In some embodiments, the zwitterionic moiety is phosphorylcholine, and at least one of $L_1$, $L_{1'}$, $L_{2'}$ and $L_{3'}$ comprises

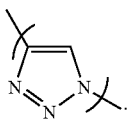

The ratio of zwitterionic moiety:agent may be from about 2:1 to about 10:1, for example, 5:1. The polymer may have a $M_w$ from about 8 kDa to about 100 kDa and a $M_n$ from about 5 kDa to about 80 kDa.

In yet another aspect, the invention generally relates to a polyester terpolymer comprising zwitterion-functionalized pendant groups and biological agent-coupled pedant groups. In some embodiments, the zwitterionic moiety may be phosphorylcholine, and the pendant groups comprise

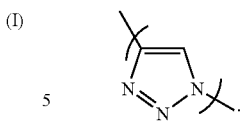

The ratio of zwitterionic moiety:agent may be from about 2:1 to about 10:1, for example, 5:1. The polymer may have a $M_w$ from about 8 kDa to about 100 kDa and a $M_n$ from about 5 kDa to about 80 kDa.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes.

EQUIVALENTS

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. The following examples contain important additional information, exemplification and guidance which can be adapted to the practice of this invention in its various embodiments and equivalents thereof.

REFERENCES

1. K. Ishihara, *Trends Polym. Sci.* 1997, 5, 401-407.
2. I. Ma, E. Lobb, N. C. Billingha$M_w$ S. P. Armes, A. L. Lewis, L. A. W. and J. Salvage, *Macromolecules*, 2002, 35, 9306-9314.
3. G. Mantovani, F. Lecolley, L. Tao, D. Haddleton, J. Clerx, J. Cornelissen, and K. Velonia. *J. Am. Chem. Soc*, 2005, 127, 2966-2973.
4. Y. Iwasaki and K. Ishihara. *Anal. Bioanal. Chem.* 2005, 381, 534-546.
5. R. Greenwald. *J. Controlled Release*. 2001, 74, 159-171.
6. R. B. Greenwald, A. Pendri, C. Conover, C. Gilbert, R. Yang and J. Xia, *J. Med. Chem.* 1996 39, 1938-1940
7. E. Ostuni, R. Chapman, R. Holmlin, S. Takayama, and G. M. Whitesides. *Langmuir,* 2001, 17, 5605-5620,
8. R. Riva, Ch. Schmeits, S. Jerome, R. Jerome and Ph. Lecomte. *Chem. Commun.*, 2005, 5334-5343.
9. L. Mespouille, M. Vachaudez, F. Suriano, P. Gerbaux, O. Coulembier, P. Degee, R. Flammang and P. Dubois. *Macromol. Rapid Commun.*, 2007, 28, 2151.
10. Ph. Lecomte, R. Riva, C. Jerome and R. Jerome. *Macromol. Rapid Commun.*, 2008. 29. 982-997.
11. B. Parrish, R. B. Breitenkamp and T. Emrick, *J. Am. Chem. Soc.*, 2005, 127, 7404-7410.
12. H. Kolb, M. G. Finn and B. Sharpless, K., *Angew. Chem. Int. Ed.*, 2001, 40, 2004-2021.
13. C. Bouillon, A. Meyer, S. Vidal, A. Jochu$M_w$ Y. Chevolot, J. P. Cloarec, J. P. Praly, J. J. Vasseur and F. Morvan, *J. Org. Chem.*, 2006, 71, 4700-4702.
14. H. Li, L. Liao and L. Lijian. *Macromol. Rapid Commun.*, 2007, 28, 411-416.

15. J. Wantanabe and K. Ishihara. *Artificial Organs.* 2003, 27, 3, 242-248.
16. Y. Iwasaki, Y. Tojo, T. Kurosaki and N. Nakabayaski, *J. Biomed. Mater. Res.* 2003, 65, 164-169.
17. F. Nederberg, T. Bowden and J. Hilborn, *Macromolecules,* 2004, 37, 954-965.
18. D. Samanta, K. Kratz, X. Zhang and T. Emrick, *Macromolecules,* 2008, 41, 530.
19. J. Xu, J. Ji, W. Chen and J. Shen, *J. Controlled Release,* 2005, 107, 502-512.
20. J. Salvage, S. Rose, G. Phillips, G. Hanlon, A. Lloyd, I. Ma, Y. Iris, S. Armes, N. Billingha$M_w$ and A. Lewis, *J. Controlled Release,* 2005, 104, 259-270.
21. S. Abraha$M_w$ S. Brahi$M_w$ K. Ishihara, and A. Guiseppi-Elie, *Biomaterials.* 2005. 26. 4767-4778.
22. Duncan, R., Polymer conjugates as anticancer nanomedicines. *Nat. Rev. Cancer* 2006, 6 (9), 688-701.
23. Vicent, M. J.; Duncan, R., Polymer conjugates: nanosized medicines for treating cancer. *Trends Biotechnol.* 2006, 24 (1), 39-47.
24. Maggon, K., R&D Paradigm shift and billion-dollar biologics. *Handbook of Pharmaceutical and Biotechnology*, John Wiley 2007, 161-198.
25. Lee, C. C.; Gillies, E. R.; Fox, M. E.; Guillaudeu, S. J.; Frechet, J. M.; Dy, E. E.; Szoka, F. C., A single dose of doxorubicin-functionalized bow-tie dendrimer cures mice bearing C-26 colon carcinomas. *Proc. Natl. Acad. Sci. USA* 2006, 103 (45), 16649-54.
26. Veronese, F. M.; Schiavon, O.; Pasut, G.; Mendichi, R.; Andersson, L.; Tsirk, A.; Ford, J.; Wu, G.; Kneller, S.; Davies, J.; Duncan, R., PEG-doxorubicin conjugates: influence of polymer structure on drug release, in vitro cytotoxicity, biodistribution, and antitumor activity. *Bioconjug. Chem.* 2005, 16 (4), 775-84.
27. Maeda, H.; Wu, J.; Sawa, T.; Matsumura, Y.; Hori, K., Tumor vascular permeability and the EPR effect in macromolecular therapeutics: a review. *J. Control. Release* 2000, 65 (1-2), 271-84.
28. Veronese, F. M.; Pasut, G. PEGylation, successful approach to drug delivery. *Drug Discov. Today* 2005, 10 (21), 1451-1458.
29. Lee, C. C.; MacKay, J. A.; Frechet, J. M. J.; Szoka, F. C. Designing dendrimers for biological applications. *Nat. Biotechnol.* 2005, 23 (12), 1517-1526.
30. Borja-Cacho, D.; Jensen, E. H.; Saluja, A. K.; Buchsbau$M_w$ D. J.; Vickers, S. M., Molecular targeted therapies for pancreatic cancer. *Am. J. Surg.* 2008, 196 (3), 430-41.
31. Yu, D.; Peng, P.; Dharap, S. S.; Wang, Y.; Mehlig, M.; Chandna, P.; Zhao, H.; Filpula, D.; Yang, K.; Borowski, V.; Borchard, G.; Zhang, Z.; Minko, T., Antitumor activity of poly(ethylene glycol)-camptothecin conjugate: the inhibition of tumor growth in vivo. *J. Control. Release* 2005, 110 (1), 90-102.
32. DeRosier, L. C.; Buchsbau$M_w$ D. J.; Oliver, P. G.; Huang, Z. Q.; Sellers, J. C.; Grizzle, W. E.; Wang, W.; Zhou, T.; Zinn, K. R.; Long, J. W.; Vickers, S. M., Combination treatment with TRA-8 anti death receptor 5 antibody and CPT-11 induces tumor regression in an orthotopic model of pancreatic cancer. *Clin. Cancer Res.* 2007, 13 (18 Pt 2), 5535s-5543s.
33. Sapra, P.; Zhao, H.; Mehlig, M.; Malaby, J.; Kraft, P.; Longley, C.; Greenberger, L. M.; Horak, I. D., Novel delivery of SN38 markedly inhibits tumor growth in xenografts, including a camptothecin-11-refractory model. *Clin. Cancer Res.* 2008, 14 (6), 1888-96.
34. Zhao, H.; Rubio, B.; Sapra, P.; Wu, D.; Reddy, P.; Sai, P.; Martinez, A.; Gao, Y.; Lozanguiez, Y.; Longley, C.; Greenberger, L. M.; Horak, I. D., Novel prodrugs of SN38 using multiarm poly(ethylene glycol) linkers. *Bioconjug. Chem.* 2008, 19 (4), 849-59.
35. Kelly, K. A.; Bardeesy, N.; Anbazhagan, R.; Gurumurthy, S.; Berger, J.; Alencar, H.; Depinho, R. A.; Mahmood, U.; Weissleder, R., Targeted nanoparticles for imaging incipient pancreatic ductal adenocarcinoma. *PLoS Med.* 2008, 5 (4), e85.
36. Zhao, H.; Lee, C.; Sai, P. K.; Choe, Y. H.; Boro, M.; Pendri, A.; Guan, S. Y.; Greenwald, R. B. 20-O-acylcamptothecin derivatives: Evidence for lactone stabilization. *J. Org. Chem.* 2000, 65 (15), 4601-4606.
37. Parrish, B.; Quansah, J. K.; Emrick, T. Functional polyesters prepared by polymerization of alpha-allyl(valerolactone) and its copolymerization with epsilon-caprolactone and delta-valerolactone. *Polym. Sci. Pol. Chem.* 2002, 40 (12), 1983-1990.
38. Parrish, B.; Emrick, T. Aliphatic polyesters with pendant cyclopentene groups: Controlled synthesis and conversion to polyester-graft-PEG copolymers. *Macromolecules* 2004, 37 (16), 5863-5865.
39. Parrish, B.; Breitenkamp, R. B.; Emrick, T. PEG- and peptide-grafted aliphatic polyesters by click chemistry. *J. Am. Chem. Soc.* 2005, 127 (20), 7404-7410.
40. Parrish, B.; Emrick, T. Soluble camptothecin derivatives prepared by click cycloaddition chemistry on functional aliphatic polyesters. *Bioconjugate Chem.* 2007, 18 (1), 263-267.
41. Chabot, G. G. Clinical pharmacokinetics of irinotecan. *Clin. Pharmacokinet.* 1997, 33 (4), 245-259.
42. Pommier, Y. Topoisomerase I inhibitors: camptothecins and beyond. *Nat. Rev. Cancer* 2006, 6 (10), 789-802.
43. Ishihara, K. New polymeric biomaterials-phospholipid polymers with a biocompatible surface. *Front. Med. Biol. Eng.* 2000, 10 (2), 83-95.
44. Iwasaki, Y.; Ishihara, K. Phosphorylcholine-containing polymers for biomedical applications. *Anal. Bioanal. Chem.* 2005, 381 (3), 534-546.
45. Matyjaszewski, K.; Xia, J. H. Atom transfer radical polymerization. *Chem. Rev.* 2001, 101 (9), 2921-2990.
46. Samanta, D.; McRae, S.; Cooper, B.; Hu, Y.; Emrick, T.; Pratt, J.; Charles, S. A. End-Functionalized Phosphorylcholine Methacrylates and their Use in Protein Conjugation. *Biomacromolecules* 2008, 9 (10), 2891-2897.
47. Geng, J.; Mantovani, G.; Tao, L.; Nicolas, J.; Chen, G. J.; Wallis, R.; Mitchell, D. A.; Johnson, B. R. G.; Evans, S. D.; Haddleton, D. M. Site-directed conjugation of "Clicked" glycopolymers to form glycoprotein mimics: Binding to mammalian lectin and induction of immunological function. *J. Am. Chem. Soc.* 2007, 129 (49), 15156-15163.
48. Haag, R.; Kratz, F., Polymer therapeutics: concepts and applications. *Angew. Chem. Int. Ed. Engl.* 2006, 45 (8), 1198-215.

What is claimed is:

1. A polymer network comprising the following monomer subunits:

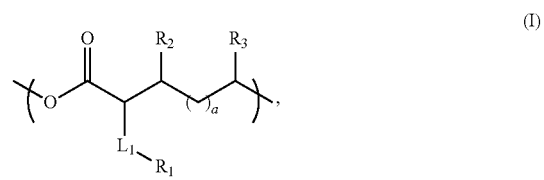

(I)

-continued

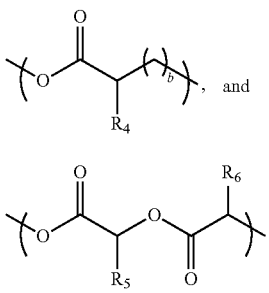

and further comprising at least one of the following monomer subunits:

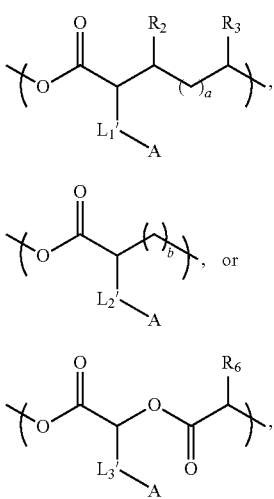

wherein

R$_1$ is a group comprising a zwitterionic moiety selected from sulfobetaine and phosphorylcholine;

R$_2$, R$_3$, R$_4$, R$_5$, R$_6$ each is independently selected from the group consisting of hydrogen and (C$_1$-C$_{15}$) alkyl;

a each is 0, 1, 2, or 3;

b each is, 1, 2, 3, 4, 5, or 6;

A is selected from camptothecin, irinotecin, SN-38, and derivatives thereof; and each of L$_1$', L$_2$' and L$_3$' is independently a linker group linked to A or R$_1$, wherein at least one of L$_1$', L$_2$' and L$_3$' comprises

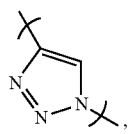

wherein the polymer network is crosslinked.

2. The polymer network of claim 1, wherein the ratio of zwitterionic moiety : A is from about 2 : 1 to about 10 : 1.

3. The polymer of claim 2, wherein the polymer has a M$_w$ from about 8 kDa to about 100 kDa and a M$_n$ from about 5 kDa to about 80 kDa.

4. The polymer network of claim 1, wherein the ratios of (I) : (II) : (III) is about (10%-60%) : (10%-60%) : (5%-40%).

5. The polymer network of claim 1, wherein each of R$_2$, R$_3$, R$_4$, R$_5$, and R$_6$ is independently selected from the group consisting of hydrogen, methyl and ethyl.

6. The polymer network of claim 1, wherein the sulfobetaine has the structure:

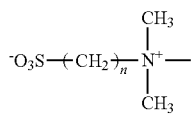

wherein n is an integer from about 1 to about 15.

* * * * *